US009492461B2

(12) United States Patent
King et al.

(10) Patent No.: US 9,492,461 B2
(45) Date of Patent: *Nov. 15, 2016

(54) METHODS AND COMPOSITIONS FOR TREATING INTERVERTEBRAL DISC HERNIATIONS

(75) Inventors: Vanja M. King, Memphis, TN (US); John M. Zanella, Cordova, TN (US); Jared Wilsey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1056 days.

This patent is subject to a terminal disclaimer.

(21) Appl. No.: 12/396,122

(22) Filed: Mar. 2, 2009

(65) Prior Publication Data

US 2009/0263459 A1    Oct. 22, 2009

Related U.S. Application Data

(63) Continuation-in-part of application No. 12/105,864, filed on Apr. 18, 2008, now Pat. No. 8,524,267.

(60) Provisional application No. 61/046,218, filed on Apr. 18, 2008.

(51) Int. Cl.
*A61L 31/16* (2006.01)
*A61K 31/573* (2006.01)
*A61P 19/00* (2006.01)

(52) U.S. Cl.
CPC .......... *A61K 31/573* (2013.01); *A61L 2430/38* (2013.01)

(58) Field of Classification Search
None
See application file for complete search history.

(56) References Cited

U.S. PATENT DOCUMENTS

| 3,190,802 | A | | 6/1965 | Zeile et al. |
|---|---|---|---|---|
| 3,020,660 | A | | 8/1965 | Zeile et al. |
| 4,624,255 | A | | 11/1986 | Schenck et al. |
| 4,765,974 | A | | 8/1988 | Tokuda et al. |
| 4,863,457 | A | | 9/1989 | Lee |
| 5,175,052 | A | | 12/1992 | Tokuda et al. |
| 5,336,505 | A | | 8/1994 | Ng et al. |
| 5,378,801 | A | * | 1/1995 | Reichert ................... B01J 19/20 528/354 |
| 5,447,947 | A | | 9/1995 | Campbell |
| 5,484,607 | A | | 1/1996 | Horacek |
| 5,522,844 | A | | 6/1996 | Johnson |
| 5,635,204 | A | | 6/1997 | Gevirtz et al. |
| 5,801,188 | A | | 9/1998 | Hassenbusch, III et al. |
| 5,868,789 | A | | 2/1999 | Huebner |
| 5,869,100 | A | | 2/1999 | Horacek |
| 5,942,503 | A | | 8/1999 | Jung et al. |
| 5,942,530 | A | | 8/1999 | Panetta et al. |
| 5,945,416 | A | | 8/1999 | Shannon et al. |
| 5,980,927 | A | | 11/1999 | Nelson et al. |
| 6,030,642 | A | | 2/2000 | Horacek |
| 6,069,129 | A | | 5/2000 | Sandberg et al. |
| 6,147,102 | A | | 11/2000 | Borgman |
| 6,179,862 | B1 | | 1/2001 | Sawhney |
| 6,287,588 | B1 | | 9/2001 | Shih et al. |
| 6,312,725 | B1 | * | 11/2001 | Wallace et al. ............... 424/484 |
| 6,331,311 | B1 | | 12/2001 | Brodbeck et al. |
| 6,417,184 | B1 | | 7/2002 | Ockert |
| 6,428,804 | B1 | | 8/2002 | Suzuki et al. |
| 6,461,631 | B1 | | 10/2002 | Dunn et al. |
| 6,468,527 | B2 | * | 10/2002 | Austin et al. .............. 424/94.64 |
| 6,534,048 | B1 | | 3/2003 | Borgman |
| 6,589,549 | B2 | | 7/2003 | Shih et al. |
| 6,630,155 | B1 | | 10/2003 | Chandrashekar et al. |
| 6,632,457 | B1 | | 10/2003 | Sawhney |
| 6,756,058 | B2 | | 6/2004 | Brubaker et al. |
| 6,758,859 | B1 | * | 7/2004 | Dang ........................ A61F 2/91 623/1.15 |
| 6,773,714 | B2 | | 8/2004 | Dunn et al. |
| 6,974,462 | B2 | | 12/2005 | Sater |
| 6,992,110 | B2 | | 1/2006 | Kranzler et al. |
| 7,144,412 | B2 | | 12/2006 | Wolf et al. |
| 7,166,570 | B2 | | 1/2007 | Hunter et al. |
| 7,220,281 | B2 | | 5/2007 | Lambrecht et al. |
| 7,229,441 | B2 | | 6/2007 | Trieu et al. |
| 7,235,043 | B2 | | 6/2007 | Gellman et al. |
| 7,318,840 | B2 | | 1/2008 | McKay |
| 7,329,259 | B2 | | 2/2008 | Cragg |
| 7,345,065 | B2 | | 3/2008 | Gil et al. |
| 7,361,168 | B2 | | 4/2008 | Makower et al. |
| 7,367,978 | B2 | | 5/2008 | Drewry et al. |
| 7,449,019 | B2 | | 11/2008 | Uchida et al. |
| 7,507,398 | B2 | | 3/2009 | Rabinowitz et al. |

(Continued)

FOREIGN PATENT DOCUMENTS

WO        03005961 A2      1/2003
WO   WO-2005-113032    *  12/2005

(Continued)

OTHER PUBLICATIONS

Reijo Autio, "MRI of Herniated Nucleus Pulposus", Acta Universities Ouluensis D Medica 877, pp. 1-75, 2006.
Atrigel, QLT, Inc., www.qltinc.com, revised Jul. 2006, QLT USA, Fort Collins, CO.
Riew, K.D. et al., "The Effect of Nerve-Root Injections on the Need for Operative Treatment of Lumbar Radicular Pain" The Journal of Bone and Joint Surgery, 2000, vol. 82-A, No. 11, pp. 1589-1593.
International Search Report and Written Opinion for International Application No. PCT/US2009/040234 mailed on Dec. 1, 2009.

*Primary Examiner* — Frederick Krass
*Assistant Examiner* — Celeste A Roney
(74) *Attorney, Agent, or Firm* — Sorell Lenna & Schmidt LLP

(57) ABSTRACT

Methods and compositions are provided for treating an intervertebral disc herniation by local administration of one or more biodegradable drug depots comprising a therapeutically effective amount of a glucocorticoid at or near the intervertebral disc herniation to reduce the size of the intervertebral disc herniation.

19 Claims, 4 Drawing Sheets

(56) References Cited

U.S. PATENT DOCUMENTS

| | | |
|---|---|---|
| 7,524,812 B2 | 4/2009 | Ellis et al. |
| 2002/0009454 A1 | 1/2002 | Boone et al. |
| 2002/0054915 A1* | 5/2002 | Goldenheim et al. ........ 424/497 |
| 2002/0058656 A1 | 5/2002 | Ockert |
| 2002/0090398 A1 | 7/2002 | Dunn et al. |
| 2002/0094998 A1 | 7/2002 | Burke et al. |
| 2002/0156532 A1* | 10/2002 | Ferree .................... 623/17.16 |
| 2003/0009227 A1* | 1/2003 | Lambrecht ........... A61B 5/1076 623/17.16 |
| 2003/0022926 A1 | 1/2003 | Lavand'Homme |
| 2003/0108588 A1* | 6/2003 | Chen et al. ................ 424/423 |
| 2003/0204191 A1 | 10/2003 | Sater et al. |
| 2003/0233136 A1* | 12/2003 | Williams et al. ............. 607/50 |
| 2004/0028726 A1 | 2/2004 | Fischer et al. |
| 2004/0072799 A1 | 4/2004 | Li et al. |
| 2004/0082540 A1 | 4/2004 | Hermida Ochoa |
| 2004/0101582 A1 | 5/2004 | Wolicki |
| 2004/0151753 A1* | 8/2004 | Chen ................... A61K 9/0024 424/426 |
| 2004/0208917 A1 | 10/2004 | Fischer et al. |
| 2004/0214793 A1 | 10/2004 | Hermida Ochoa |
| 2004/0265364 A1 | 12/2004 | Ozturk et al. |
| 2005/0058696 A1 | 3/2005 | Donello et al. |
| 2005/0059744 A1 | 3/2005 | Donello et al. |
| 2005/0095277 A1 | 5/2005 | Ozturk et al. |
| 2005/0142163 A1 | 6/2005 | Hunter et al. |
| 2005/0186261 A1 | 8/2005 | Avelar et al. |
| 2005/0197293 A1 | 9/2005 | Mellis et al. |
| 2006/0073182 A1* | 4/2006 | Wong et al. .................. 424/426 |
| 2006/0106361 A1 | 5/2006 | Muni et al. |
| 2006/0148903 A1 | 7/2006 | Burch et al. |
| 2006/0189944 A1 | 8/2006 | Campbell et al. |
| 2007/0156180 A1 | 7/2007 | Jaax et al. |
| 2007/0185497 A1 | 8/2007 | Cauthen et al. |
| 2007/0202074 A1 | 8/2007 | Shalaby |
| 2007/0243225 A1 | 10/2007 | McKay |
| 2007/0243228 A1 | 10/2007 | McKay |
| 2008/0091207 A1 | 4/2008 | Truckai et al. |
| 2008/0152709 A1 | 6/2008 | Bortz |
| 2008/0171075 A1 | 7/2008 | Ozturk et al. |
| 2008/0175911 A1 | 7/2008 | McKay et al. |
| 2008/0213283 A1 | 9/2008 | Olmarker et al. |
| 2008/0294261 A1 | 11/2008 | Pauza et al. |
| 2008/0317805 A1 | 12/2008 | McKay et al. |

FOREIGN PATENT DOCUMENTS

| | | |
|---|---|---|
| WO | 2006011915 A1 | 2/2006 |
| WO | 2006022611 A2 | 3/2006 |
| WO | 2006101540 A1 | 9/2006 |
| WO | WO-2006-138690 * | 12/2006 |
| WO | 2008079868 A1 | 7/2008 |
| WO | 2009100441 A2 | 8/2009 |

* cited by examiner

METHODS AND COMPOSITIONS FOR TREATING INTERVERTEBRAL DISC HERNIATIONS

This application claims the benefit of the filing date of Provisional Application No. 61/046,218 filed Apr. 18, 2008, entitled "Fluocinolone Formulations In A Biodegradable Polymer Carrier" and U.S. application Ser. No. 12/105,864 filed Apr. 18, 2008, entitled "Dexamethasone Formulations In A Biodegradable Material." These entire disclosures are hereby incorporated by reference into the present disclosure.

BACKGROUND

Intervertebral disc herniation is a troublesome disorder of the spinal column, which can cause pronounced pain and muscle dysfunction, and be debilitating to the patient. Pain from intervertebral disc herniation can last as long as six months and, in very severe cases, for years.

The spinal column is composed of a series of connected bones called vertebrae, which surround the spinal cord and protect it from damage. Nerves branch off the spinal cord and travel to the rest of the body, allowing for communication between the brain and the body. Vertebrae of the spine are connected by spongy intervertebral discs and two small joints called facet joints. The intervertebral discs and facet joints rest between the vertebrae and together allow movement of the vertebrae.

The intervertebral disc is made up of strong connective tissues that hold one vertebra to the next and acts as a cushion or shock absorber between the vertebrae. The intervertebral disc is composed of a tough outer layer called the annulus fibrosus and a gel-like center called the nucleus pulposus. The annulus fibrosus is a strong radial tire-like structure made up of lamellae; concentric sheets of collagen fibers connected to the vertebral end plates. The annulus fibrosus encloses the gel-like nucleus pulposus.

A herniated intervertebral disc can be caused by a sudden back injury or by gradual wear and tear of the disc (also called disc degeneration). As people get older, the center of the disc may start to lose water content, making the disc less effective as a cushion. As a disc deteriorates, the annulus fibrosus can also tear. This can allow displacement of the nucleus pulposus through a crack in the annulus fibrosus, into the space occupied by the nerves and spinal cord. The herniated disc can then press on the nerves (also called pinched nerve) and cause pain, numbness, tingling or weakness in the extremities.

Intervertebral disc herniations may occur in any disc in the spine but herniations in the lumbar and the cervical spine are most common. Disc herniations in the cervical spine may cause radiating pain and muscle dysfunction in the arm, which is generally referred to as cervical rhizopathy. While disc herniations in the lumbar spine may induce radiating pain and muscle dysfunction in the leg, which is generally referred to as sciatica.

Treatments for intervertebral disc herniations include anti-inflammatory medications, such as steroids and non-steroid anti-inflammatory drugs (NSAIDs), physical therapy, behavior modification, intradiscal electrothermal therapy (IDET) and surgery. The surgery can be performed as either an open or mini-open surgery, using very small opening incisions or percutaneously, utilizing specially designed instruments and radiographic techniques.

When herniated discs are surgically treated to remove the herniated portion of the disc annulus, relieving pressure on the spinal nerves, the annulus integrity becomes compromised. This will often result in an annulus fibrosis that may re-herniate, or more likely, will leak nucleus pulposus from the nucleus of the disc, through the weakened zone of the annulus fibrosis, onto the nerve complex surrounding and adjacent to the disc. The nucleus pulposus generates a highly inflammatory response around the exposed nerve complex and causes continued discogenic pain. This phenomenon, sometimes called induced leaky disc syndrome, is a common side effect for procedures that remove the herniated portion of the disc annulus.

There is still a need for new compositions and methods to treat intervertebral disc herniation and the pain and/or inflammation associated with this debilitating condition. New compositions and methods that reduce the size of the disc herniation by enhancing nucleus pulposus resorption would be most beneficial.

SUMMARY

New compositions and methods are provided that effectively reduce, prevent or treat intervertebral disc herniations. In various embodiments, glucocorticoid compositions and methods are provided that reduce the size of the herniation in a single drug depot or multiple drug depots. New glucocorticoid compositions and methods are provided, which can easily allow accurate and precise implantation of a drug depot containing the glucocorticoid with minimal physical and psychological trauma to a patient. One advantage of the glucocorticoid drug depot compositions and methods is that the drug depot can now be easily delivered to the target tissue site (e.g., at the nucleus pulposus, or near the spinal column, etc.) and reduce, prevent or treat the intervertebral disc herniation. In this way, accurate and precise implantation of the drug depot in a minimally invasive procedure to treat the disc herniation can be accomplished.

In one embodiment, a method is provided of treating vertebral disc herniation in a patient in need of such treatment, the method comprising administering one or more biodegradable drug depots comprising a therapeutically effective amount of a glucocorticoid at or near the vertebral disc herniation, wherein the one or more biodegradable drug depot is capable of releasing an effective amount of the glucocorticoid over a period of at least 3 days to six months. In some embodiments, the glucocorticoid can be released from the drug depot for about 6 weeks to about 3 months.

In another embodiment, an implantable drug depot useful for treating vertebral disc herniation in a patient in need of such treatment is provided, the implantable drug depot comprising a therapeutically effective amount of a glucocorticoid, the depot being implantable at or near the vertebral disc herniation, wherein the drug depot is loaded with about 0.5 weight % to about 40 weight % of the glucocorticoid and is capable of releasing an effective amount of a glucocorticoid over a period of at least 3 days to 8 weeks.

In yet another embodiment, a method is provided for reducing the size of a vertebral disc herniation in a patient, the method comprising administering one or more biodegradable drug depots comprising fluocinolone at or near the vertebral disc herniation, wherein the one or more biodegradable drug depot is capable of releasing fluocinolone over a period of at least 3 days to two months to reduce the size of the vertebral disc herniation by at least 50%.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1A:
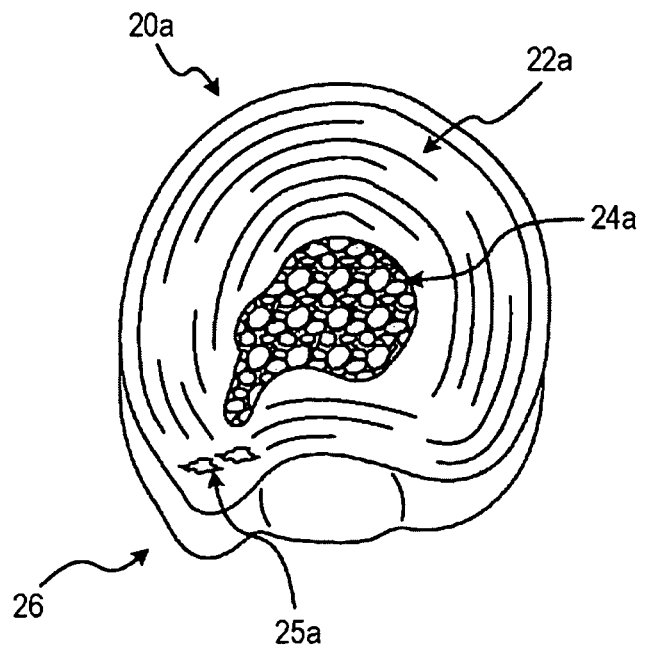
FIG. 1A is a cross-sectional view of a target tissue site, which is a herniated intervertebral disc where the disc has not ruptured.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

New compositions and methods are provided that effectively reduce, prevent or treat intervertebral disc herniation. In various embodiments, glucocorticoid compositions and methods are provided that reduce the size of the herniation in a single drug depot or multiple drug depots. New glucocorticoid compositions and methods are provided, which can easily allow accurate and precise implantation of a drug depot containing the glucocorticoid with minimal physical and psychological trauma to a patient. One advantage of the glucocorticoid drug depot compositions and methods is that the drug depot can now be easily delivered to the target tissue site (e.g., at the nucleus pulposus, or near the spinal column, etc.) and reduce, prevent or treat the intervertebral disc herniation. In this way, accurate and precise implantation of the drug depot in a minimally invasive procedure to treat the disc herniation can be accomplished.

In one embodiment, a method is provided of treating vertebral disc herniation in a patient in need of such treatment, the method comprising administering one or more biodegradable drug depots comprising a therapeutically effective amount of a glucocorticoid at or near the vertebral disc herniation, wherein the one or more biodegradable drug depot is capable of releasing an effective amount of the glucocorticoid over a period of at least 3 days to six months.

In another embodiment, a method is provided that utilizes one or more drug depots that release an effective amount of the fluocinolone or dexamethasone or a pharmaceutically acceptable salt thereof over a period of at least 1 week to 6 weeks to reduce, prevent or inhibit intervertebral disc herniation.

Glucocorticoids

A glucocorticoid is contained in a drug depot. A drug depot comprises a physical structure to facilitate sustained release of the drug in a desired site (e.g., a disc space, a spinal canal, a disc herniation of the patient, etc.). The drug depot also comprises the drug. The term "drug" as used herein is generally meant to refer to any substance that alters the physiology of the patient. The term "drug" may be used interchangeably herein with the terms "therapeutic agent", "therapeutically effective amount", and "active pharmaceutical ingredient" or "API". It will be understood that a "drug" formulation may include more than one therapeutic agent, wherein exemplary combinations of therapeutic agents include a combination of two or more drugs. The drug depot provides a concentration gradient of the therapeutic agent around the depot for delivery to the site. In various embodiments, the drug depot provides an optimal drug concentration gradient of the therapeutic agent at a distance of up to about 0.1 cm to about 5 cm from the implant site.

A "therapeutically effective amount" or "effective amount" is such that when administered, the drug results in alteration of the biological activity, such as, for example, inhibition of inflammation, reduction or alleviation of pain, reduction or improvement in the condition, etc. In various embodiments, the therapeutically effective amount of a glucocorticoid is that amount that prevents, reduces or treats intervertebral disc herniation.

In some embodiments, the dose of glucocorticoid can be administered locally at a low dose of not to exceed 100 micrograms/kg/day. In some embodiments, the dosage range may be from about 100 micrograms/kg/day to about 1 pg/kg/day. In some embodiments, the glucocorticoid can be administered at a dose of about 50 micrograms/kg/day to about 100 pg/kg/day or about 30 micrograms/kg/day to about 500 pg/kg/day. It will be understood that the dosage administered to a patient can be as single depot or multiple depots depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired.

Glucocorticoids are a class of steroids characterized by an ability to bind with the glucocorticoid receptor. Glucocorticoids have a broad spectrum of anti-inflammatory and immunosuppressive effects. They act by inhibiting leukocyte traffic; interfering with functions of leukocytes, fibroblasts, and endothelial cells; and suppressing the synthesis and actions of inflammatory cytokines including interleukin-6. Glucocorticoids affect glucose metabolism. The glucocorticoids used herein have at least some glucocorticoid activity and optionally may have some mineralocorticoid activity.

As used herein "glucocorticoid" encompasses a glucocorticoid or pharmaceutically acceptable salts thereof; pharmacologically-active derivatives of the glucocorticoid or an active metabolite of the glucocorticoid. As used herein, "pharmaceutically acceptable salts" refer to derivatives of the disclosed compounds (e.g., esters or amines) wherein the parent compound may be modified by making acidic or basic salts thereof. Examples of pharmaceutically acceptable salts include, but are not limited to, mineral or organic acid salts of basic residues such as amines; alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, or nitric acids; or the salts prepared from organic acids such as acetic, fuoric, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, methanesulfonic, ethane disulfonic, oxalic, isethionic acid. Pharmaceutically acceptable also includes the racemic mixtures ((+)-R and (−)-S enantiomers) or each of the dextro and levo isomers of the glucocorticoid individually. The glucocorticoids may be in the free acid or base form or be pegylated for long acting activity. In some embodiments, the glucocorticoid is in the stearate form.

A suitable glucocorticoid, includes but is not limited to, alclometasone, aldosterone amcinonide, 21-acetoxypregnenolone, algestone, amcinonide, beclomethasone, betamethasone, budesonide, beclometasone, budesonide, ciclesonide, clobetasol, clobetasone, clocortolone, cloprednol, cortivazol, chloroprednisone, corticosterone, cortisone, deflazacort, deoxycorticosterone, desonide, desoxycortone, desoximetasone, dexamethasone, dexamethasone acetate, dexamethasone phosphate di-sodium salt, diflorasone, diflucortolone, difluprednate, enoxolone, fluazacort, flumethasone, flunisolide, fluocinolone, fluocinolone acetonide or stearate, fluperolone acetate, fluprednidene acetate, fluprednisolone, flurandrenolide, fluticasone propionate, fluclorolone, fludrocortisone, fludroxycortide, flumetasone, flunisolide, fluocinonide, fluocortin, fluocortolone, fluorometholone, fluperolone, fluprednidene, fluticasone, formocortal, halcinonide, halometasone, halobetasol propionate, halopredone acetate, hydrocortamate, hydrocortisone, hydrocortisone aceponate, hydrocortisone buteprate, hydrocortisone butyrate, loteprednol, loteprednol etabonate, mazipredone, medrysone, meprednisone, mometasone furoate, medrysone, meprednisone, methylprednisolone, methylprednisolone aceponate, mometasone furoate, paramethasone, prednicarbate, prednisone, prednisolone, prednylidene, paramethasone, prednicarbate, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, ulobetasol or pharmaceutically acceptable salts or esters or amines thereof or a combination thereof.

Glucocorticoids are distinguished from mineralocorticoids and sex steroids by their specific receptors, target cells, and effects. For example, on one hand, mineralocorticoids exert their effect on the kidneys, causing selective excretion of excess potassium in the urine and at the same time conservation and/or retention of sodium. On the other hand, sex steroids such as the female hormones estrogen and progesterone and the male androgens such as testosterone are used for male/female development.

In one exemplary embodiment, to prevent, reduce or treat intervertebral disc herniation, the glucocorticoid comprises fluocinolone or a pharmaceutically acceptable salt thereof. Some examples of potential pharmaceutically acceptable salts include those salt-forming acids and bases that do not substantially increase the toxicity of the compound, such as, salts of alkali metals such as magnesium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like. To the extent that salts of fluocinolone can be created for safe administration to a mammal, they are within the scope of the application herein. Further, when referring to fluocinolone the active ingredient may not only be in the salt form, but also in the base form (e.g., free acid), amine, ester or racemic forms or a combination thereof.

Fluocinolone

Fluocinolone is available from various pharmaceutical manufacturers. In various embodiments, the fluocinolone comprises fluocinolone acetonide. The dosage of fluocinolone may be from approximately 0.0005 to approximately 100 μg/kg/day. Additional dosages of fluocinolone include from approximately 0.0005 to approximately 95 µg/kg/day; approximately 0.0005 to approximately 90 µg/kg/day; approximately 0.0005 to approximately 85 µg/kg/day; approximately 0.0005 to approximately 80 µg/kg/day; approximately 0.0005 to approximately 75 µg/kg/day; approximately 0.001 to approximately 70 µg/kg/day; approximately 0.001 to approximately 65 µg/kg/day; approximately 0.001 to approximately 60 µg/kg/day; approximately 0.001 to approximately 55 µg/kg/day; approximately 0.001 to approximately 50 µg/kg/day; approximately 0.001 to approximately 45 µg/kg/day; approximately 0.001 to approximately 40 µg/kg/day; approximately 0.001 to approximately 35 µg/kg/day; approximately 0.0025 to approximately 30 µg/kg/day; approximately 0.0025 to approximately 25 µg/kg/day; approximately 0.0025 to approximately 20 µg/kg/day; and approximately 0.0025 to approximately 15 µg/kg/day. In another embodiment, the dosage of fluocinolone is from approximately 0.005 to approximately 15 µg/kg/day. In another embodiment, the dosage of fluocinolone is from approximately 0.005 to approximately 10 µg/kg/day. In another embodiment, the dosage of fluocinolone is from approximately 0.005 to approximately 5 µg/kg/day. In another embodiment, the dosage of fluocinolone is from approximately 0.005 to 2.5 µ/kg/day. In some embodiments, the amount of fluocinolone is between 0.001 and 600 µg/day. In some embodiments, the amount of fluocinolone is between 0.0025 and 400 µg/day. In some embodiments, the fluocinolone load in one or more drug depots can be 0.5 wt. % to 20 wt. %.

In some embodiments, fluocinolone may be released from the depot at a dose of about 10 pg to about 10 mg/hr, about 100 pg/hr to about 1 mg/hr, about 1 ng/hr to about 100 ug/hr, about 10 ng/hr to about 10 ug/hr, about 100 ng/hr to about 1 ug/hr or about 500 ug/hr. In various embodiments, the dose may be pulse doses from about 10 pg to about 10 mg/day, or about 100 pg/day to about 0.02 mcg/day.

Figure 4:
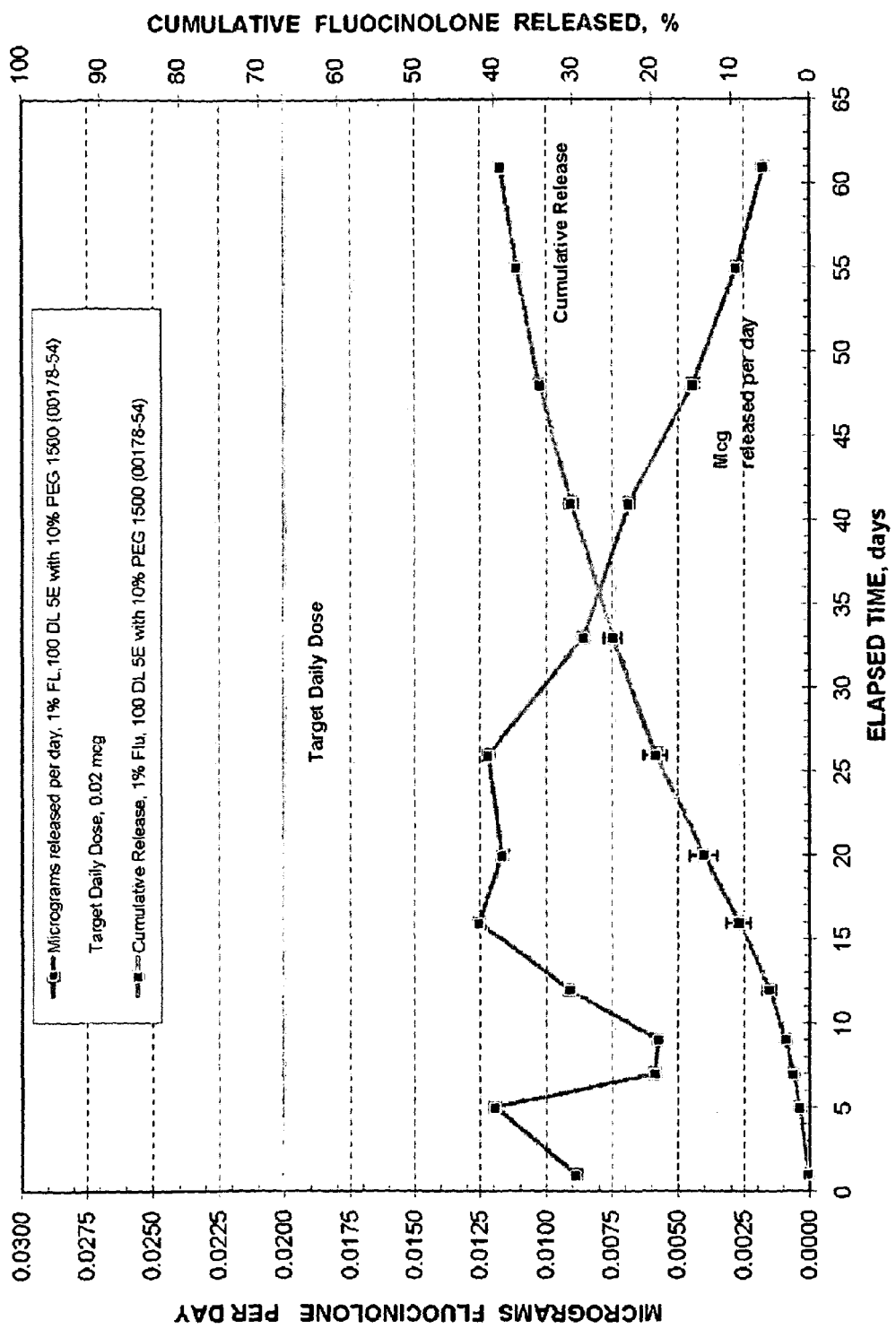
FIG. 4 is a graphic representation of in vitro % cumulative release of fluocinolone depots over 60 days and graphic representations of the micrograms of fluocinolone released from the drug depot per day.

FIG. 4 is a graphic representation of in vitro % cumulative release profile of a drug depot containing 1% fluocinolone. The drug depot elutes 0.0025 to about 0.0125 mcg/day for over 60 days and releases at least 40% of fluocinolone loaded in the drug depot over 60 days. Suitable fluocinolone depots for use in the present application are described in Provisional Application No. 61/046,218 filed Apr. 18, 2008, entitled "Fluocinolone Formulations In A Biodegradable Polymer Carrier".

Dexamethasone

In one exemplary embodiment, to prevent, reduce or treat intervertebral disc herniation, the glucocorticoid comprises dexamethasone. When referring to dexamethasone, unless otherwise specified or apparent from context it is understood that the inventors are also referring to pharmaceutically acceptable salts. Some examples of potentially pharmaceutically acceptable salts include those salt-forming acids and bases that do not substantially increase the toxicity of the compound, such as, salts of alkali metals such as magnesium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like. To the extent that salts of dexamethasone can be created for safe administration to a mammal, they are within the scope of the present application. When referring to dexamethasone unless otherwise specified, the specification also includes dexamethasone acetate and/or dexamethasone sodium phosphate.

Further, when referring to dexamethasone the active ingredient may not only be in the salt form, but also in the base form (e.g., free acid). In various embodiments, if it is in the acid form, it may be combined with polymers under conditions in which there is not severe polymer degradation, as may be seen upon heat or solvent processing that may occur with PLGA or PLA. In various embodiments, the drug depot comprises from about 5 wt. % to 20 wt. % dexamethasone acetate and the polymer comprises 75/25 or 85/25 PLGA, POE, or SAIB, with or without mPEG.

Dexamethasone is available from various manufacturers. In various embodiments, dexamethasone may be released from the depot at a dose of about 10 pg to about 10 mg/hr, about 100 pg/hr to about 1 mg/hr, about 1 ng/hr to about 100 ug/hr, about 10 ng/hr to about 10 ug/hr, about 100 ng/hr to about 1 ug/hr or about 500 ug/hr. In various embodiments, the dose may be about 0.01 to about 10 mg/kg/day or about 1 mg to about 120 mg/day. Suitable dexamethasone depots for use in the present application are described in U.S. application Ser. No. 12/105,864 filed Apr. 18, 2008, entitled "Dexamethasone Formulations In A Biodegradable Material."

In addition to the glucocorticoids, the drug depot may comprise one or more additional therapeutic agents. Examples of therapeutic agents include, those that are direct- and local-acting modulators of pro-inflammatory cytokines such as TNF-α and IL-1 including, but not limited to, soluble tumor necrosis factor α receptors, any pegylated soluble tumor necrosis factor α receptor, monoclonal or polyclonal antibodies or antibody fragments or combinations thereof. Examples of suitable therapeutic agents include receptor antagonists, molecules that compete with the receptor for binding to the target molecule, antisense polynucleotides, and inhibitors of transcription of the DNA encoding the target protein. Suitable examples include, but are not limited to, Adalimumab, Infliximab, Etanercept, Pegsunercept (PEG sTNF-R1), sTNF-R1, CDP-870, CDP-571, CNI-1493, RDP58, ISIS 104838, 1→3-β-D-glucans, Lenercept, PEG-sTNFRII Fc Mutein, D2E7, Afelimomab, and combinations thereof. In other embodiments, a therapeutic agent includes metalloprotease inhibitors, glutamate antagonists, glial cell-derived neurotropic factors (GDNF), B2 receptor antagonists, Substance P receptor (NK1) antagonists such as capsaicin and civamide, downstream regulatory element antagonistic modulator (DREAM), iNOS, inhibitors of tetrodotoxin (TTX)-resistant Na+-channel receptor subtypes PN3 and SNS2, inhibitors of interleukins such as IL-1, IL-6 and IL-8, and anti-inflammatory cytokines, TNF binding protein, onercept (r-hTBP-1), recombinant adeno-associated viral (rAAV) vectors encoding inhibitors, enhancers, potentiators, or neutralizers, antibodies, including, but not limited to, naturally occurring or synthetic, double-chain, single-chain, or fragments thereof. For example, suitable therapeutic agents include molecules that are based on single chain antibodies called Nanobodies™ (Ablynx, Ghent Belgium), which are defined as the smallest functional fragment of a naturally occurring, single-domain antibody. Alternatively, therapeutic agents include agents that effect kinases and/or inhibit cell signaling mitogen-activated protein kinases (MAPK), p38 MAPK, Src or protein tyrosine kinase (PTK). Therapeutic agents include, kinase inhibitors such as, for example, Gleevec, Herceptin, Iressa, imatinib (STI571), herbimycin A, tyrphostin 47, erbstatin, genistein, staurosporine, PD98059, SB203580, CNI-1493, VX-50/702 (Vertex/Kissei), SB203580, BIRB 796 (Boehringer Ingelheim), Glaxo P38 MAP Kinase inhibitor, RWJ67657 (J&J), UO126, Gd, SCIO-469 (Scios), RO3201195 (Roche), Semipimod (Cytokine PharmaSciences), or derivatives thereof.

Therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-II (which modulate TNF-α receptor expression), and aurin-tricarboxylic acid (which inhibits TNF-α), for example, may also be useful as therapeutic agents for reducing inflammation. It is contemplated that where desirable a pegylated form of the above may be used. Examples of other therapeutic agents include NF kappa B inhibitors such as, clonidine; antioxidants, such as dilhiocarbamate, and other compounds, such as, for example, bupivacaine, or sulfasalazine.

Specific examples of therapeutic agents suitable for use include, but are not limited to an anti-inflammatory agent, analgesic agent, or osteoinductive growth factor or a combination thereof. Anti-inflammatory agents include, but are not limited to, salicylates, diflunisal, sulfasalazine, indomethacin, ibuprofen, ketorolac, naproxen, tolmetin, diclofenac, ketoprofen, fenamates (mefenamic acid, meclofenamic acid), enolic acids (piroxicam, meloxicam), celecoxib, etodolac, nimesulide, apazone, sulindac or tepoxalin; antioxidants, such as dithiocarbamate, or other compounds such as sulfasalazine [2-hydroxy-5-[-4-[C2-pyridinylamino)sulfonyl]azo]benzoic acid] or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof.

Analgesics also include agents with analgesic properties, such as for example, amitriptyline, carbamazepine, gabapentin, pregabalin, clonidine, or a combination thereof.

The depot may contain a muscle relaxant. Exemplary muscle relaxants include by way of example and not limitation, alcuronium chloride, atracurium bescylate, baclofen, carbolonium, carisoprodol, chlorphenesin carbamate, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The depot comprises the therapeutic agent or agents and may also contain other non-active ingredients or excipients. It has a multi-functional purpose including the carrying, stabilizing and controlling the release of the therapeutic agent(s). The controlled release process, for example, may be by a solution-diffusion mechanism or it may be governed by an erosion-controlled process. Typically, the depot will be a solid or semi-solid formulation comprised of a biocompatible material, which can be biodegradable. The term "solid" is intended to mean a rigid material, while, "semi-solid" is intended to mean a material that has some degree of flexibility, thereby allowing the depot to bend and conform to the surrounding tissue requirements. Some examples of excipients include, for example, mPEG (methoxypolyethyleneglycol), sorbitol, D-sorbitol, maltodextrin, cyclodextrin, B-cyclodextrin, or combinations thereof. The excipients may be added in weight percentages from 0.5% to 50%.

In various embodiments, the depot material will be durable within the tissue site for a period of time equal to (for biodegradable components) or greater than (for non-biodegradable components) the planned period of drug delivery. For example, the depot material may have a melting point or glass transition temperature close to or higher than body temperature, but lower then the decomposition or degradation temperature of the therapeutic agent. However, the pre-determined erosion of the depot material can also be used to provide for slow release of the loaded therapeutic agent(s).

In various embodiments, the drug depot may be designed to release the glucocorticoid when certain trigger points are reached (e.g., temperature, pH, etc.) after implantation in vivo. For example, the drug depot may comprise polymers that will release more drug as the body temperature reaches greater than, for example, 102° F., particularly if the drug possesses antipyretic properties such as a glucocorticoid. In various embodiments, depending on the site of implantation, the drug depot may release more or less drug as a certain pH is reached. For example, the drug depot may be designed to release the drug as the bodily fluid having a certain pH contact the drug depot (e.g., CSF having a pH of about 7.35 to about 7.70, blood having a pH of about 7.35 to about 7.45, etc.)

In various embodiments, the depot may have a high drug loading, such that the glucocorticoid and/or other therapeutic agent comprises about 20-99 wt % of the depot, or 20-95 wt % of the depot, or 50-95 wt % of the depot. In various embodiments, the amount of glucocorticoid and/or other therapeutic agent are present in the depot in a range from about 0.1% to about 40% by weight of the depot (including 0.1%, 0.2%, 0.5%, 1%, 2%, 3%, 4%, 5%, 6%, 7%, 8%, 9%, 10%, 11%, 12%, 13%, 14%, 15, %, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, and ranges between any two of these points, for instance, 0.1-10%, 10-20% and 20-30%, etc.). In various embodiments, the glucocorticoids can be loaded in the drug depot at a range of 0.5-20%.

In one exemplary embodiment, with drug loads of 1% to 20% fluocinolone, 100 DL, 85/15 PLGA or DL-PLA or DL-PLA, 50/50 PLGA mixture can be added in an amount of from about 10% to 99%.

In some embodiments, there is a drug depot comprising fluocinolone and a polymer, wherein the polymer comprises poly(lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone or a combination thereof.

In one exemplary embodiment, with drug loads of 5% to 20% dexamethasone base or acetate, 85/15 PLGA or 75/25 PLGA, or POE, or SAIB can be added in an amount of from about 10% to 98%. As persons of ordinary skill in the art are aware, when implantable elastomeric depot compositions having a blend of polymers with different end groups are used the resulting formulation will have a lower burst index and a regulated duration of delivery. For example, one may use polymers with acid (e.g., carboxylic acid) and ester end groups (e.g., lauryl, methyl or ethyl ester end groups).

In various embodiments, the drug depot may release approximately 0.005 to approximately 10 µg/kg/day of a glucocorticoid for a total of at least one day to 6 months, or 1 to 8 weeks or 2 to 6 weeks to reduce, prevent, or treat intervertebral disc herniations.

In various embodiments, the drug depot releases 5%, 10%, 15%, 20%, 25%, 30%, 40%, 50%, 60%, 70%, 80%, 90%, 95%, or 99% of a glucocorticoid over a period of 3 days to six months, or 1 to 6 weeks after the drug depot is administered at or near the intervertebral herniation to reduce, prevent or treat intervertebral disc herniations. The drug depot may have a "release rate profile" that refers to the percentage of active ingredient that is released over fixed units of time, e.g., mcg/hr, mg/hr, mcg/day, mg/day, 10% per day for one week, ten days, etc. As persons of ordinary skill know a release rate profile may be but need not be linear and may be continuous pulse dosing.

In some embodiments, the drug depot may not be biodegradable. For example, the drug depot may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. Typically, these types of drug depots may need to be removed after a certain amount of time.

In some instances, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

A "depot" includes, but is not limited to, capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions. The drug depot may comprise a pump that holds and administers the pharmaceutical. In some embodiments, the drug depot has pores that allow release of the drug from the depot. The drug depot will allow fluid in the depot to displace the drug. However, cell infiltration into the depot will be prevented by the size of the pores of the depot. In this way, in some embodiments, the depot should not function as a tissue scaffold and allow tissue growth. Rather, the drug depot will solely be utilized for drug delivery. In some embodiments, the pores in the drug depot will be less than 250 to 500 microns. This pore size will prevent cells from infiltrating the drug depot and laying down scaffolding cells. Thus, in this embodiment, drug will elute from the drug depot as fluid enters the drug depot, but cells will be prevented from entering. In some embodiments, where there are little or no pores, the drug will elute out from the drug depot by the action of enzymes, by hydrolytic action and/or by other similar mechanisms in the human body.

Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "biodegradable" includes that all or parts of the drug depot will degrade over time by the action of enzymes, by hydrolytic action and/or by other similar mechanisms in the human body. In various embodiments, "biodegradable" includes that depot (e.g., microparticle, microsphere, gel, etc.) can break down or degrade within the body to non-toxic components after or while a therapeutic agent has been or is being released. By "bioerodible" it is meant that the depot and/or gel will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

In various embodiments, the depot may comprise a bioabsorbable, bioerodible, and/or a biodegradable biopolymer that may provide immediate release, sustained release or controlled release of the drug. Examples of suitable sustained release biopolymers include, but are not limited to, poly (alpha-hydroxy acids), poly (lactide-co-glycolide) (PLGA), polylactide (PLA), polyglycolide (PG), polyethylene glycol (PEG), PEG 200, PEG 300, PEG 400, PEG 500, PEG 550, PEG 600, PEG 700, PEG 800, PEG 900, PEG 1000, PEG 1450, PEG 3350, PEG 4500, PEG 8000, conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, ,-caprolactone, D,L-lactide-ε-caprolactone, D,L-lactide-glycolide-ε-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) hydroxypropyl cellulose, hydroxypropyl methylcellulose, hydroxyethyl methylcellulose, carboxymethylcellulose or salts thereof, Carbopol, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, polyvinyl alcohols, propylene glycol, or combinations thereof.

In various embodiments, when the drug depot comprises a polymer, it may be employed at about 0.5 wt % to about 99 wt % or at about 10 wt % to about 99 wt % or about 30 wt % to about 60 wt % based on the weight of the drug depot.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt %, and more typically within the range of 0-30 wt %. If the depot is to be placed in the spinal area or joint area, in various embodiments, the depot may comprise sterile preservative free material.

The depot can be different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a sphere, a cylinder such as a rod or pellet, fiber, a flat surface such as a disc, film, or sheet, or the like. Flexibility may be a consideration so as to facilitate placement of the drug depot. In various embodiments, the drug depot can be different sizes, for example, the drug depot may be a length of from about 0.5 mm to 5 mm and have a diameter of from about 0.01 to about 2 mm. In various embodiments, the drug depot may have a layer thickness of from about 0.005 to 1.0 mm, such as, for example, from 0.05 to 0.75 mm.

Radiographic markers can be included on the drug depot to permit the user to accurately position the depot into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium, and/or metal beads or particles. Where present, the radiographic marker is typically present in an amount of from about 10% to about 40% (including 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% and 40%, as well as ranges between any two of these values, e.g., 10-15%, 15-20%, 20-25%, 25-30%, 30-35%, 35-40%, and so fourth, with 15-30% being more typical, even more typically 20-25%). In various embodiments, the radiographic marker could be a spherical shape or a ring around the depot.

In one exemplary embodiment, a drug depot for delivering a therapeutic agent to a target tissue site beneath the skin of a patient is provided, the drug depot comprising an effective amount of a glucocorticoid, wherein the target tissue site comprises at least one spinal disc, spinal foraminal space near the spinal nerve root, facet or synovial joint, or spinal canal.

In one exemplary embodiment, an implantable drug depot useful for reducing, preventing or treating intervertebral disc herniations in a patient in need of such treatment is provided, the implantable drug depot comprising a therapeutically effective amount of fluocinolone or dexamethasone or a pharmaceutically acceptable salt thereof, the depot being implantable at a site beneath the skin to reduce, prevent or treat intervertebral disc herniations, wherein the drug depot comprises (i) about 0.5 weight % to about 40 weight % of the fluocinolone or dexamethasone or a pharmaceutically acceptable salt thereof; (ii) about 60 weight % to about 99% of a polymer; and optionally (iii) 1% to 50% of an excipient; where the drug depot is capable of releasing an effective amount of fluocinolone or dexamethasone or pharmaceutically acceptable salt thereof over a period of at least 3 days to 6 months, or 1 week to 8 weeks or from 1 week to 6 weeks. In various embodiments, the polymer comprises PLGA, DL-PLA, or a combination thereof and the excipient comprises mPEG, D-sorbitol, maltodextrin, PEG, cyclodextrin or a combination thereof.

In various embodiments, the drug depot comprises a gel, which includes a substance having a gelatinous, jelly-like, or colloidal properties at room temperature. The gel, in various embodiments, may have the glucocorticoid and optionally one or more additional therapeutic agents dispersed throughout it or suspended within the gel. The dispersal of the therapeutic agent may be even throughout the gel. Alternatively, the concentration of the therapeutic agent may vary throughout it. As the biodegradable material of the gel or drug depot degrades at the site, the therapeutic agent (e.g., glucocorticoid) is released.

When the drug depot is a gel, in contrast to a sprayable gel that typically employs a low viscosity polymer, a gel with a higher viscosity may be desirable for other applications, for example, a gel having a putty-like consistency may be more preferable for intervertebral disc herniation.

In another exemplary embodiment, the gel is in viscous form is loaded with one or more drug depots (e.g., microspheres loaded with a therapeutic agent), wherein the viscous gel is positioned into a synovial joint, disc space, a spinal canal, or a soft tissue surrounding the spinal canal of a subject. The gel can also be used, in various embodiments, to seal or repair tissue as well as reduce, prevent or treat intervertebral disc herniations. In yet another exemplary embodiment, the gel is injectable, and/or an adherent gel that solidifies upon contact with tissue. For example, the gel may be administered as a liquid that gels in situ at the target tissue site. In various embodiments, the gel can comprise a two part system where a liquid is administered and a gelling agent is added subsequently to cause the liquid to gel or harden.

In various embodiments, the gel is a hardening gel, where after the gel is applied to the target site, it hardens and the drug can be released as the bodily fluid contacts the gel.

In various embodiments, the drug depot is loaded with a glucocorticoid and optionally one or more additional therapeutic agents, and delivered to the desired target tissue site (e.g., degenerative disc, spinal canal, epidural space, etc.) and, in various embodiments, the drug depot may be held in place by a suture, barb, staple, adhesive gel, etc. which prevents the drug depot from being removed from that site by the venous systemic circulation or otherwise dispersed too widely, which reduces the desired therapeutic effect. For example, after hours or days, the drug depot may degrade, thereby allowing the drug depots (e.g., microspheres) to begin releasing the therapeutic agent. The microspheres may not begin releasing the agent until they are released from the drug depot. So, the microspheres may be formed from an insoluble or inert substances, but soluble or active once it comes into contact with the target tissue site. Likewise, the drug depot may comprise a substance that dissolves or disperses within the tissue. As the drug depot begins to dissolve within hours to days, the drug depots (e.g., microspheres) are exposed to body fluids and begin releasing their contents. The drug depot can be formulated to optimize exposure time of the drug depot and release of the therapeutic agent from the drug depot.

In various embodiments, the drug depot (e.g., gel) is flowable and can be injected, sprayed, instilled, and/or dispensed to, on or in the target tissue site. "Flowable" means that the gel formulation is easy to manipulate and may be brushed, sprayed, dripped, injected, shaped and/or molded at or near the target tissue site as it coagulates. "Flowable" includes formulations with a low viscosity or water-like consistency to those with a high viscosity, such as a paste-like material. In various embodiments, the flowability of the formulation allows it to conform to irregularities, crevices, cracks, and/or voids in the tissue site. For example, in various embodiments, the gel may be used to fill one or more voids in the spinal column.

In various embodiments, the drug depot comprises poly (alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters, polyaspirins, polyphosphagenes, collagen, starch, pregelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, ,-caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG (poly(d,l-lactide-co-glycolide), PLA-PLGA, poloxamer 407, PEG-PLGA-PEG triblock copolymers, SAIB (sucrose acetate isobutyrate) or combinations thereof. These one or more components allow the therapeutic agent to be released from the drug depot in a controlled and/or sustained manner. For example, the drug depot containing the therapeutic agent and a polymer matrix can be injected at the target tissue site and the polymer matrix breaks down over time (e.g., hours, days) within the target tissue site releasing a glucocorticoid and optionally additional therapeutic agents. Thus the administration of the drug depot can be localized and occur over a period of time (e.g., at least one day to about 1 to 8 weeks or longer).

The terms "sustained release" (e.g., extended release or controlled release) are used herein to refer to one or more therapeutic agent(s) that is introduced into the body of a human or other mammal and continuously releases a stream of one or more therapeutic agents over a predetermined time period and at a therapeutic level sufficient to achieve a desired therapeutic effect throughout the predetermined time period. Reference to a continuous release stream is intended to encompass release that occurs as the result of biodegradation in vivo of drug depot, or a matrix or component thereof, or as the result of metabolic transformation or dissolution of the therapeutic agent(s) or conjugates of therapeutic agent(s).

In various embodiments, the drug depot can be designed to cause an initial burst dose of therapeutic agent within the first 24 hours after implantation. "Initial burst" or "burst effect" or "bolus dose" refers to the release of therapeutic agent from the drug depot during the first 24 hours after the drug depot comes in contact with an aqueous fluid (e.g., synovial fluid, cerebral spinal fluid, etc.). In various embodiments, the drug depot is designed to avoid this initial burst effect.

In various embodiments, the drug depot contains one or more different release layer(s) that releases a bolus dose of a glucocorticoid or pharmaceutically acceptable salt thereof (e.g., 5 mg to 60 mg at a target site beneath the skin) and one or more sustain release layer(s) that releases an effective amount of a glucocorticoid or pharmaceutically acceptable salt thereof over a period of, for example, 1 to 8 weeks. In various embodiments, the one or more immediate release layer(s) comprise PLGA, which degrades faster and than the one or more sustain release layer(s), which comprises PLA, which degrades at a slower rate than the PLGA.

In various embodiments, when the drug depot comprises a gel, the gel may have a pre-dosed viscosity in the range of about 1 to about 500 centipoise (cps), 1 to about 200 cps, or 1 to about 100 cps. After the gel is administered to the target site, the viscosity of the gel will increase and the gel will have a modulus of elasticity (Young's modulus) in the range of about $1 \times 10^4$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In one embodiment, the gel may be an adherent gel, which comprises a therapeutic agent that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The gel may also adhere to the targeted tissue site not only by chemical processes, but also by a mechanical interdigitation with the tissue prior to hardening.

The gel may, for example, solidify upon contact with the targeted tissue or after deployment from a targeted delivery system. The targeted delivery system may be, for example, a syringe, a catheter, needle or cannula or any other suitable device. The targeted delivery system may inject or spray the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or adhere to the target tissue.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in the spine).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances, for example when applying the formulation via spray.

In various embodiments, the molecular weight of the gel can be varied by many methods known in the art. The choice of method to vary molecular weight is typically determined by the composition of the gel (e.g., polymer, versus non-polymer). For example, in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel, which includes a high molecular weight polymer, tends to coagulate or solidify more quickly than a polymeric composition, which includes a low-molecular weight polymer. Polymeric gel formulations, which include high molecular weight polymers, also tend to have a higher solution viscosity than a polymeric gel, which includes a low-molecular weight polymer.

In various embodiments, the gel can have a viscosity of about 300 to about 5,000 centipoise (cp). In other embodiments, the gel can have a viscosity of from about 5 to about 300 cps, from about 10 cps to about 50 cps, from about 15 cps to about 75 cps at room temperature, which allows it to be sprayed at or near the target site.

In various embodiments, the drug depot may comprise material to enhance viscosity and control the release of the drug. Such material may include, for example, hydroxypropyl cellulose, hydroxypropyl methylcellulose, hydroxyethyl methylcellulose, carboxymethylcellulose and salts thereof, Carbopol, poly(hydroxyethylmethacrylate), poly(methoxyethylmethacrylate), poly(methoxyethoxy-ethylmethacrylate), polymethyl-methacrylate (PMMA), methylmethacrylate (MMA), gelatin, polyvinyl alcohols, propylene glycol, PEG 200, PEG 300, PEG 400, PEG 500, PEG 550, PEG 600, PEG 700, PEG 800, PEG 900, PEG 1000, PEG 1450, PEG 3350, PEG 4500, PEG 8000 or combinations thereof. For example, in various embodiments, the drug depot comprises a polymer containing PLGA, DL-PLA, or a combination thereof and the excipient comprises mPEG, D-sorbitol, maltodextrin, 10% to 60% PEG 3350 MW, cyclodextrin or a combination thereof.

In various embodiments, the drug depot comprises poly (lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone, glycolide-caprolactone or a combination thereof.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and longer degradation time). Typically, a gel with a high molecular weight provides a stronger matrix and the matrix takes more time to degrade. In contrast, a gel with a low molecular weight degrades more quickly and provides a softer matrix. In various embodiments, the gel has a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, and about 0.80 to about 1.00 dL/g. In various embodiments, the drug depot may have an inherent viscosity as from about 0.05 to about 1.0 dL/g.

The drug depot release profile can also be controlled, among other things, by controlling the particle size distribution of the components of the drug depot. In various embodiments, the particle size distribution of the components of the drug depot (e.g., a glucocorticoid, gel, etc.) may be in the range of from about 10 μm to 100 μm so that the drug depot can easily be delivered to or at or near the target site by injection, spraying, instilling, etc.

In various embodiments, the drug depot may comprise a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing since they are more likely to be biodegradable and biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agent into the drug depot, microspheres may be dispersed within the drug depot, the microspheres loaded with the therapeutic agent (e.g., glucocorticoid). In one embodiment, the microspheres provide for a sustained release of the therapeutic agent. In yet another embodiment, the drug depot, which is biodegradable, prevents the microspheres from releasing the therapeutic agent; the microspheres thus do not release the therapeutic agent until they have been released from the depot. For example, a drug depot may be deployed around a target tissue site (e.g., a nerve root). Dispersed within the drug depot are a plurality of microspheres that encapsulate the desired therapeutic agent. Certain of these microspheres degrade once released from the drug depot, thus releasing the therapeutic agent.

Microspheres, much like a fluid, may disperse relatively quickly, depending upon the surrounding tissue type, and hence disperse the therapeutic agent. In some situations, this may be desirable; in others, it may be more desirable to keep the therapeutic agent tightly constrained to a well-defined target site.

Cannula or Needle

It will be appreciated by those with skill in the art that the depot can be administered to the target site (e.g., at or near the herniated disc) using a cannula or needle that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Coumand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflammed nerve root and the drug depot implanted at this site for treating the condition. Typically, the transforaminal approach involves approaching the intervertebral space through the intervertebral foramina.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 22 gauge. In various embodiments the gauge of the needle or cannula is about 18 to about 22 gauge.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, calcium, and/or metal beads or particles.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

The drug depot, and/or medical device to administer the drug may be sterilizable. In various embodiments, one or more components of the drug depot, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot and/or one or more components of the device, including, but not limited to, gas sterilization, such as, for example, with ethylene oxide or steam sterilization.

In various embodiments, a kit is provided that may include additional parts along with the drug depot and/or medical device combined together to be used to implant the drug depot (e.g., ribbon-like fibers). The kit may include the drug depot device in a first compartment. The second compartment may include a canister holding the drug depot and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. Each tool may be separately packaged in a plastic pouch that is radiation sterilized. A cover of the kit may include illustrations of the implanting procedure and a clear plastic cover may be placed over the compartments to maintain sterility.

Drug Delivery

In various embodiments, a method for delivering a glucocorticoid at or near a herniated disc of a patient is provided, the method comprising inserting a cannula at or near the herniated disc and implanting the drug depot containing a glucocorticoid locally at or near the herniated disc of the patient. In various embodiments, to administer the drug depot to the desired site, first the cannula or needle can be inserted through the skin and soft tissue down to the target tissue site at or near the herniated disc and the drug depot administered (e.g., injected, implanted, instilled, sprayed, etc.) at or near the target site. In those embodiments where the drug depot is separate from the gel, first the cannula or needle can be inserted through the skin and soft tissue down to the site of injection and one or more base layer(s) of gel can be administered to the target site (e.g., herniated disc). Following administration of the one or more base layer(s), the drug depot can be implanted on or in the base layer(s) so that the gel can hold the depot in place or reduce migration. If required a subsequent layer or layers of gel can be applied on the drug depot to surround the depot and further hold it in place. Alternatively, the drug depot may be implanted first and then the gel placed (e.g., brushed, dripped, injected, or painted, etc.) around the drug depot to hold it in place. By using the gel, accurate and precise implantation of a drug depot can be accomplished with minimal physical and psychological trauma to the patient. In various embodiments, the drug depot can be sutured to the target site or alternatively the drug depot can be implanted, without suturing. For example, in various embodiments, the drug depot can be a ribbon shaped depot and placed at the target site (e.g., herniated disc), before, during or after surgery.

In various embodiments, when the target tissue site comprises a spinal region, a portion of fluid (e.g., spinal fluid, etc.) can be withdrawn from the target site through the cannula or needle first and then the depot administered (e.g., placed, dripped, injected, or implanted, etc.). The target site will re-hydrate (e.g., replenishment of fluid) and this aqueous environment will cause the drug to be released from the depot.

"Localized" delivery includes, delivery where one or more drugs are deposited within, at or near a tissue (e.g., herniated disc). For example, localized delivery includes delivery to a nerve root of the nervous system or a region of the brain, or in close proximity (within about 0.1 cm to 10 cm, for example) thereto. "Targeted delivery system" provides delivery of one or more drugs depots (e.g., gels or depot dispersed in the gel, etc.) having a quantity of therapeutic agent that can be deposited at or near the target tissue site (e.g., herniated disc) as needed for prevention, reduction, or treatment of intervertebral disc herniation.

Intervertebral Disc Herniation

Intervertebral disc herniation can occur anywhere in the spine, such as the cervical spine (the neck), the thoracic spine (the part of the back behind the chest), the lumbar spine (lower back), and sacral spine (the part connected to the pelvis that does not move). In embodiments claimed herein, the drug depot can be implanted at or near the disc herniation, for example, at the cervical, thoracic, lumbar, and/or sacral vertebrae.

As used herein "intervertebral disc herniation" includes local displacement of disc material beyond the limits of the intervertebral disc space. The disc material may be nucleus pulposus, cartilage, fragmented apophysical bone, annular tissue or any combination thereof. Displacement of disc material may put pressure on the exiting spinal nerve and/or cause an inflammatory reaction leading to radiculopathy, weakness, numbness, and/or tingling in the arms or legs. Radiculopathy refers to any disease affecting the spinal nerve roots.

Intervertebral herniation can lead to conditions such as for example, sciatica, a compressed nerve, discogenic back pain, foraminal stenosis, pinched nerve, compressive neuropathy, chronic nerve pain, sensory and/or motor neuropathy, numbness or weakness, or the like. Thus, the drug depot of the present application can be used to treat these conditions.

In some embodiments, intervertebral disc herniation includes a rupture of the annulus fibrosis, through which the inner disc material (nucleus pulposus) extrudes, protrudes, bulges, migrates and/or re-herniates. Sometimes disc extrusions may be displaced so much that it has lost continuity with the parent disc. When this happens the extrusion is called sequestration. Thus, the drug depot of the present application can be used to treat ruptures, protrusions, bulges, extrusions, re-herniation, and migration, fragmented, and/or sequestrated nucleus pulposus.

A "migrated disc or fragmented disc" refers to displacement of the disc material away from an opening in the annulus through which material has extruded. Sometimes migrated fragments will be sequestrated. For example, the nucleus pulposus may migrate away from the herniated disc so that there is sequestration in a different location in the spine that may lead to pinched nerve or spinal stenosis.

In general, most intervertebral disc herniation takes place in the lumbar area of the spine. Lumbar disc herniation occurs 15 times more often than cervical disc herniation, and it is one of the most common causes of lower back pain. The cervical discs are affected 8% of the time and the upper-to-mid-back (thoracic) discs only 1-2% of the time. Sometimes herniated discs can lead to compression of the nerve roots of the spine resulting in very painful neurological symptoms. Nerve roots (large nerves that branch out from the spinal cord) may become compressed resulting in neurological symptoms, such as sensory or motor changes. For example herniation of the nucleus pulposus often is accompanied by lower back pain that worsens in the sitting position and pain that radiates to the lower extremities. The radiating pain, for example, in sciatica is often described as dull, burning or sharp pain, accompanied by intermittent sharp electric shock sensation, numbness, and tingling, motor or sensory defects of the respective nerve root and/or reflex abnormalities.

In some embodiments, by implanting the drug depot containing the glucocorticoid at or near the disc herniation where the nucleus pulposus extrudes, protrudes or migrates out of the annulus, the glucocorticoid as it elutes out of the drug depot causes enhanced resorption of the nucleus pulposus and reduces the size and volume of the nucleus pulposus herniation. In some embodiments, the size of the nucleus pulposus herniation is reduced and resorption is enhanced by about 15-20%, 20-25%, 25-30%, 30-35%, 35-40%, 45-50%, 55-60%, 65-70%, 75-80%, 85-90%, or 95-100% or the herniated intervertebral disc completely resolves.

In some embodiments, by administering the glucocorticoid, enhanced resorption of normal spontaneous resorption of the nucleus pulposus can occur by 15-20%, 20-25%, 25-30%, 30-35%, 35-40%, 45-50%, 55-60%, 65-70%, 75-80%, 85-90%, or 95-100% above the amount that would occur due to normal spontaneous nucleus pulposus resorption without treatment with a glucocorticoid. For example, sometimes herniated nucleus pulposus will spontaneously resorb by itself without treatment. This typically can take about six weeks to eight weeks. By administering the glucocorticoid at or near the intervertebral herniation, in some embodiments of the present application, the resorption of the nucleus pulposus will be enhanced or increase so that the herniation will heal faster than without any treatment.

In some embodiments, by implanting the drug depot at or near the disc herniation, the size and/or volume of the nucleus pulposus herniation is reduced by $1/5$, $1/4$, $1/3$, $1/2$, $2/3$, ¾ or completely. For example, the drug depot can be implanted within the herniation, 0.1 cm, 0.5 cm, 1 cm, 2 cm, 3 cm, 4 cm, 5 cm away from the disc herniation and the size and/or volume will decrease by ⅕, ¼, ⅓, ½, ⅔, ¾ or completely within a certain time period (e.g., 3 days to 6 months, 3 days to 8 weeks, or 6 weeks to 3 months).

In some embodiments, it has been found that the closer the drug depot is implanted to the intervertebral disc herniation, there will be an enhanced resorption of the nucleus pulposus and the herniation will be reduced in size and/or volume, which can lead to improvement of the patient's condition (see Example 1). This finding is contrary to conventional wisdom that steroids inhibit nucleus pulposus resorption by inhibiting macrophages, fibrogenesis, angiogenesis, wound contraction and/or altering the inflammatory response and thus inhibiting wound healing. To the contrary, Applicants find that by administering a drug depot containing a glucocorticoid (e.g., fluocinolone) the nucleus pulposus resorption is enhanced and the size and/or volume of the intervertebral disc herniation can be reduced.

In some embodiments, the glucocorticoid will reverse, reduce, and/or inhibit the progression and/or severity of intervertebral disc herniation, or reduce the severity of one or more symptoms of intervertebral disc herniation (e.g., pain, numbness, tingling, motor or sensory defects, etc.).

In some embodiments, the reduction of the intervertebral disc herniation (e.g., by enhanced nucleus pulposus resorption) can be determined clinically by improvement in the patient's signs and symptoms (e.g., reduced back pain, numbness, etc.). In some embodiments, the reduction of the intervertebral disc herniation can be determined by measuring size and/or volume reduction of the nucleus pulposus by diagnostic tests such as for example, x-ray, CT, MRI, myelogram, electromyogram, nerve conduction studies, or the like.

In some embodiments, a method is provided for treating intervertebral disc herniation in a patient in need of such treatment, the method comprising administering one or more biodegradable drug depots comprising a therapeutically effective amount of a glucocorticoid at or near the intervertebral disc herniation, wherein the one or more biodegradable drug depot is capable of releasing an effective amount of the glucocorticoid over a period of at least 3 days to 6 months.

Figure 1B:
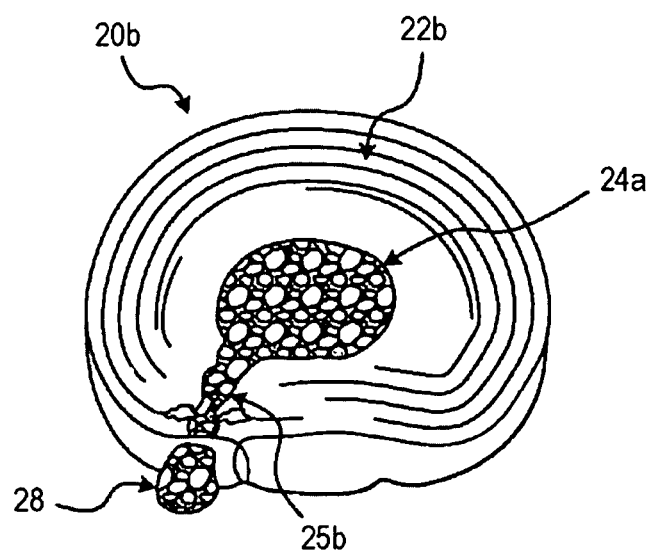
FIG. 1B is a cross-sectional view of a target tissue site, which is a herniated intervertebral disc where the disc has ruptured.

For purposes of illustration only, FIG. 1A illustrates an example of an intervertebral disc 20a. The intervertebral disc 20a is made up of two components: the annulus fibrosus 22a and the nucleus pulposus 24a. The nucleus pulposus 24a is the inner gelatinous material surrounded by the annulus fibrosus. It distributes mechanical loads placed upon the disc 20a, while the annulus fibrosus 22a provides structural integrity and constrains the nucleus pulposus 24a to a specific spinal region. The annulus fibrosus 22a is designed with fibrocartilaginous and fibrous tissue arranged in concentric layers called laminae. As one moves, from the nucleus pulposus to the periphery, the annulus fibrosus tissue becomes denser, stronger, less elastic, less fluid, and more ligamentous until reaching the outermost layers. There, the tissue actually becomes a tough, capsular ligament. The annulus fibrosus 22a can become weaker with age, and may begin to tear. As shown in FIG. 1A, defects in the annulus fibrosus called annular tears, 22a allow bulging or herniation 26 of the nucleus pulposus in the early stages. As time progresses, as shown in FIG. 1B, it often leads to a complete rupturing 28 of the annulus fibrosus 22a and 22b. The herniated 20a or ruptured 20b disc compresses the spinal canal and exerts pressure on the nerve roots that pass through the disc 20a, 20b causing lower back pain. In addition, the nucleus pulposus 24a contains significant amounts of substances capable of exciting, or increasing the excitability of, sensory nerves such as prostaglandin E, histamine-like substances, lactic acid and polypeptide amines. These substances may escape through the annular tears 28, increasing the lower back pain, sciatica, or resulting in radiating leg pain. In addition, the annular tears 25a and 25b cause fibrous tissue to grow in the tear, which increases pain and/or inflammation.

A drug depot containing the glucocorticoid can be implanted at or near the herniation. For example, at or near the annular tear. This will enhance nucleus pulposus resorption and cause the size and the volume of the herniation to decrease and/or completely resolve.

Figure 2:
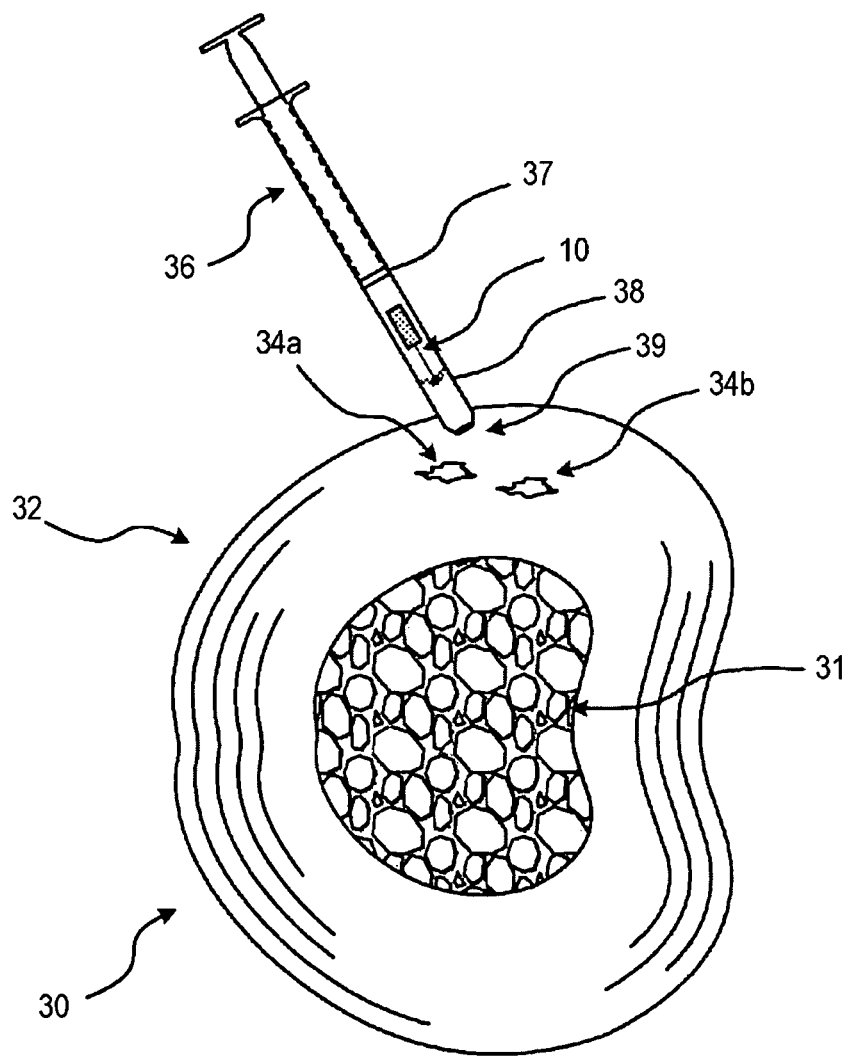
FIG. 2 is a cross-sectional view illustrating one embodiment of the implantable drug depot having an anchor attached to the drug depot by a line (e.g., suture, yarn, etc.) that is being administered into an intervertebral disc having an annulus.

FIG. 2 illustrates an intervertebral disc 30 having annular tears 34a and 34b in annulus fibrosis 32. However, this intervertebral disc is not ruptured, as the nucleus pulposus 31 is contained at this stage as a result of the implantation of the drug depot. The drug depot 10 is delivered (via a syringe 36 through a needle 38 using plunger 37) into tissue adjacent to tears 34a and 34b. The drug depot may be injected into the tissue within about 1 cm, 2 cm, or 5 cm or 10 cm of the defect, where depot will catch the adjacent tissue 39 and the depot will be at or near the annular tears 34a and 34b. In this way, target directed delivery of the drug can be accomplished.

In some embodiments, the closer the drug depot is delivered to the herniation, the more the enhancement of nucleus pulposus resorption will occur and the more there will be a reduction in intervertebral disc herniation. "Reducing intervertebral disc herniations" refers to administering a composition so as to cause a reduction in the number of intervertebral disc herniations, extent of intervertebral disc herniations (e.g., area), and/or severity of intervertebral disc herniations (e.g., thickness, volume) relative to the number, extent, and/or severity of intervertebral disc herniations that would occur without such administration. In various embodiments, reducing intervertebral disc herniations may be part of a protocol and also include performing a procedure (e.g., subsequent surgery to reduce intervertebral disc herniations). The composition or procedure may inhibit formation of intervertebral disc herniation following an intervertebral disc herniation promoting stimulus, may inhibit progression of intervertebral disc herniation, and/or may inhibit recurrence of intervertebral disc herniation.

"Preventing intervertebral disc herniations" refers to administering a therapeutic composition prior to formation of intervertebral disc herniations in order to reduce the likelihood that intervertebral disc herniations will form in response to a particular insult, stimulus, or condition. In various embodiments, preventing intervertebral disc herniations may be part of a protocol and also include performing a procedure (e.g., surgery to reduce intervertebral disc herniations). It will be appreciated that "preventing intervertebral disc herniations" does not require that the likelihood of intervertebral disc herniation formation is reduced to zero. Instead, "preventing intervertebral disc herniations" refers to a clinically significant reduction in the likelihood of intervertebral disc herniation formation following a particular insult or stimulus, e.g., a clinically significant reduction in the incidence or number of intervertebral disc herniations in response to a particular intervertebral disc herniation promoting insult, condition, or stimulus.

"Treating intervertebral disc herniations," refers to administering a composition that reverses (completely or partially), alleviates, reduces, and/or inhibits the progression and/or severity of intervertebral disc herniations, or reduces the likelihood of recurrence and/or the severity of recurrent intervertebral disc herniations. "Treating intervertebral disc herniations" also refers to administering a composition that reverses, alleviates, reduces, inhibits the progression of, or reduces the likelihood of recurrence and/or severity of one or more symptoms of intervertebral disc herniations (e.g., pain, tingling, sciatica, etc.). In various embodiments, treating intervertebral disc herniations may be part of a protocol and also include performing a procedure (e.g., surgery to reduce intervertebral disc herniations). Thus "treating intervertebral disc herniations" involves administering a therapeutic composition and/or procedure once intervertebral disc herniation(s) have already formed following an insult or stimulus.

The term "pain" includes nociception and the sensation of pain, both of which can be assessed objectively and subjectively, using pain scores and other methods well-known in the art. Exemplary types of pain reducible, preventable or treatable by the methods and compositions disclosed herein include, without limitation, lower back pain, neck pain, leg pain, radicular pain, neuropathic pain of the arm, neck, back, lower back, leg, or related pain distributions resulting from disc or spine surgery.

Although the spinal site is shown, as described above, the drug depot can be delivered to any site beneath the skin, including, but not limited to, at least one muscle, ligament, tendon, cartilage, spinal disc, spinal foraminal space, near the spinal nerve root, or spinal canal. In various embodiments, the drug depot containing a glucocorticoid can be administered to the patient parenterally. The term "parenteral" as used herein refers to modes of administration, which bypass the gastrointestinal tract, and include for example, localized intravenous, intramuscular, continuous or intermittent infusion, intraperitoneal, intrasternal, subcutaneous, intra-operatively, intrathecally, intradiscally, peridiscally, epidurally, perispinally, intraarticular injection or combinations thereof.

Parenteral administration may additionally include, for example, an infusion pump that locally administers a pharmaceutical composition (e.g., glucocorticoid) through a catheter near the spine or one or more inflamed joints, an implantable mini-pump that can be inserted at or near the target site, an implantable controlled release device or sustained release delivery system that can release a certain amount of the composition continuously per hour or in intermittent bolus doses. One example of a suitable pump for use is the SynchroMed® (Medtronic, Minneapolis, Minn.) pump. This pump has three sealed chambers. One contains an electronic module and battery. The second contains a peristaltic pump and drug reservoir. The third contains an inert gas, which provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, at specific times, or at set intervals between deliveries.

Potential drug delivery devices suitable for adaptation for the methods described herein include but are not limited to those described, for example, in U.S. Pat. No. 6,551,290 (assigned to Medtronic, the entire disclosure is herein incorporated by reference), which describes a medical catheter for target specific drug delivery; U.S. Pat. No. 6,571,125 (assigned to Medtronic, the entire disclosure is herein incorporated by reference), which describes an implantable medical device for controllably releasing a biologically active agent; U.S. Pat. No. 6,594,880 (assigned to Medtronic, the entire disclosure is herein incorporated by reference), which describes an intraparenchymal infusion catheter system for delivering therapeutic agents to selected sites in an organism; and U.S. Pat. No. 5,752,930 (assigned to Medtronic, the entire disclosure is herein incorporated by reference), which describes an implantable catheter for infusing equal volumes of agents to spaced sites. In various embodiments, pumps may be adapted with a pre-programmable implantable apparatus with a feedback regulated delivery, a micro-reservoir osmotic release system for controlled release of chemicals, small, light-weight devices for delivering liquid medication, implantable microminiature infusion devices, implantable ceramic valve pump assemblies, or implantable infusion pumps with a collapsible fluid chamber. Alzet® osmotic pumps (Durect Corporation, Cupertino, Calif.) are also available in a variety of sizes, pumping rates, and durations suitable for use in the described methods. In various embodiments, a method for delivering a therapeutic agent into a surgery site of a patient is provided. For example, the implantable Alzet® osmotic pump delivers the steroid locally to the target tissue site on a continuous basis (e.g., the Alzet® osmotic pump allows a continuous infusion in microgram/hr delivery of the glucocorticoid intrathecally near the sciatic nerve).

In various embodiments, because the glucocorticoid is locally administered, therapeutically effective doses may be less than doses administered by other routes (oral, topical, etc.). For example, the drug dose delivered from the drug depot may be, for example, 10%, 20%, 30%, 40%, 50%, 60%, 70%, 80%, 90%, 95%, 99%, or 99.9% less than the oral dosage or injectable dose. In turn, systemic side effects, such as for example, liver transaminase elevations, hepatitis, liver failure, myopathy, constipation, etc. may be reduced or eliminated.

The term "patient" refers to organisms from the taxonomy class "mammalian," including, but not limited to, humans, other primates such as chimpanzees, apes orangutans and monkeys, rats, mice, cats, dogs, cows, horses, etc.

Method of Making Glucocorticoid Depots

In various embodiments, the drug depot comprising the glucocorticoid can be made by combining a biocompatible polymer and a therapeutically effective amount of a glucocorticoid or pharmaceutically acceptable salt thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: a glucocorticoid and other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: a glucocorticoid, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, a glucocorticoid tromethamine may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the glucocorticoid containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., a glucocorticoid), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of the glucocorticoid, because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, extrusion processes may be used to form the drug depot comprising the biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., ribbon, pellet, strip, etc.) is cooled. Examples of cooling processes include air cooling and/or immersion in a cooling bath. In some embodiments, a water bath is used to cool the extruded depot. However, where a water-soluble therapeutic agent such as a glucocorticoid is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired.

In various embodiments, the drug depot can be prepared by mixing or spraying the drug with the polymer and then molding the depot to the desired shape. In various embodiments, a glucocorticoid is used and mixed or sprayed with the polymer, and the resulting depot may be formed by extrusion and dried.

Having now generally described the invention, the same may be more readily understood through the following reference to the following examples, which are provided by way of illustration and are not intended to limit the present invention unless specified.

EXAMPLES

Example 1

Purpose: To determine the effect of a fluocinolone-eluting PLA polymer pellet on NP resorption.

Summary:

Nucleus Pulposus (NP) from coccygeal (tail) disks were harvested from 15 donor female Sprague-Dawley rats and implanted into the abdominal subcutaneous space of 15 recipient female Sprague Dawley rats. The NP from 8 coccygeal disks of each donor rat was pooled for implantation as a single mass (one NP mass implant per recipient). The 15 recipients were randomly divided into 3 groups. One group received a 0.88 wt % fluocinolone pellet (10 wt % PEG 1500, in 100 DL PLA 5E, 2.0 mm length×0.5 mm diameter) in the same sub-cutaneous pocket as the NP implant. A second group received a fluocinolone (Flu) pellet of the same specifications in a separate subcutaneous pocket 1.5 cm (edge to edge) from the pocket containing the NP. The final group received a control PLA pellet in a separate subcutaneous pocket 1.5 cm from the pocket containing the NP. The Flu pellet used in this study is expected to elute approximately 0.01 μg/day of fluocinolone, based on in vitro data. Approximately 72 hours after surgical placement of the NP and pellets, animals were humanely euthanized by $CO_2$ asphyxiation and the NP was explanted from 4 animals in each of the three groups for assessing NP resorption. One animal in each of the three groups was randomly selected for histological analysis. The % mass of the ectopic NP remaining at the end point was applied as an index of resorption rate.

Results and Conclusions: The apparent NP resorption rate tended to be higher in the animals that received the fluocinolone pellets. This finding was contrary to our a priori research hypothesis (i.e., that fluocinolone may inhibit NP resorption). The percent of ectopic NP remaining on day 3 was 20.78±5.25% in the group in which the Flu pellet was placed in the same pocket as the NP, 32.38±5.71% in the group in which the Flu pellet was placed 1.5 cm away from the NP, and 40.00±5.33% in the control pellet group. While the numbers of animals in each group is too small to draw definitive conclusions, a theoretical comparison was made between the control group and the same-pocket Flu group. The difference between these two groups, when compared in isolation, did reach statistical significance ($p=0.04$). The overall histolological findings are consistent with the known effects of fluocinolone with respect to inflammation. Namely, the animal from the same-pocket Flu group dedicated for histology had a reduced inflammatory response as compared to the control pellet group. This assessment includes the size of the inflammatory pseudocapusule and the number of non-macrophage inflammatory cells inside of and adjacent to this capsule. The group in which the Flu pellet was placed in a separate pocket had an intermediate inflammatory response. However, the number of macrophages in the remaining NP appeared to be elevated in the animals receiving a Flu pellet (more so in the animal receiving a Flu pellet in the same pocket as the NP). This curious finding suggests that macrophagic activity may be responsible for the increased NP resorption rates in the animals receiving Flu pellets. However, the inverse relationship between overall inflammatory response and macrophagic activity cannot be explained with the available data. Histology was also performed on sections of the pockets 1.5 cm contralateral to the NP pockets. Histological findings in these secondary pockets were consistent with normal wound healing and did not appear to be affected by Flu pellets or control pellets (when compared to the sham incision). Fluocinolone was unable to be detected in the plasma of any animals (LLD 0.05 ng/mL).

Detailed Example 1

Fluocinolone is a corticosteroid with anti-inflammatory properties, and this study was intended to explore these properties with the ultimate aim of understanding fluocinolone's role in disk herniation healing. After disk herniation, the natural history of a sequestered herniated nucleus pulposus is to resorb partially or completely over the course of 3-6 months. It was hypothesized that fluocinolone may reduce resorption of NP (nucleus pulposus) by disrupting the immuno-inflammatory response believed to be responsible for this resorption process. The current study evaluated the effect of subcutaneous pellet implants releasing fluocinolone on NP resorption rates (as compared to control pellets). This was evaluated in a pilot study using 1) the weight of NP that is retrieved after 3 days of implantation and 2) histopathological evaluation of the surrounding tissue of both pockets in a subset of animals. NP was removed from 8 tail disks of a donor rat and implanted into a subcutaneous pocket of a recipient rat. The treatment groups included animals implanted with fluocinolone-releasing pellets in the same pocket as the NP or in a distant pocket (1.5 cm away) to evaluate penetrance of fluocinolone. Control pellets were implanted in one group. Retrieval of the pellets was done at the time of necropsy. The pellets were expected to be stable over the course of 72 hours. They were designed to last for several months, disintegrating after 4-6 months. The results from this study indicated that there was a trend toward increased resorption 3-days post-implantation when the fluocinolone pellet was together with NP in the same pocket. By comparison, there was reduced resorption when a control pellet was present in a different pocket placed 1.5 cm from the NP pocket. The group of animals with the fluocinolone pellet in a distant pocket showed intermediate results for the % of NP remaining after 3 days. The histological findings seemed to correlate with these results, with the least amount of inflammatory infiltrate surrounding the NP when the fluocinolone was together in the same pocket and the greatest amount of inflammatory response in the animal implanted with the control pellet.

Experimental Procedures
Animals

A total of up to 34 female Sprague-Dawley rats were included in this study. Thirty (30) animals were on study and four (4) rats were available to serve as spares. The rats were specific pathogen free and approximately 200 g upon arrival at the vivarium.

Receipt, Health Evaluation and Acclimatization

Upon receipt, the rats were unpacked and placed in cages. A visual health inspection was performed on each animal to include evaluation of the coat, extremities, and orifices for abnormal signs in posture and movement. None of the rats were found to be abnormal. The rats were acclimated for approximately one week prior to beginning surgery.

Environment

The rats were housed in a vivarium in clear polycarbonate plastic cages. The bedding material was irradiated corn-cob bedding (Enrich-O-Cob, The Andersons, Maumee, Ohio, USA) that was changed as frequently as needed to provide the animals with dry bedding. The room number in which the rats were housed throughout the study period was detailed in the study records. The room was supplied with HEPA filtered air. The room was on a 12-hour light/dark cycle (light hours being approximately 0600 to 1800).

Food and Water

Animals had ad libitum access to a pellet diet (Certified Pico). The manufacturer for each batch of diet supplied a certificate of analysis detailing the levels and/or concentrations of specific heavy metals, aflatoxin, organophosphates, and specific nutrients. The Certificates of Analysis (CA) were retained.

Deionized water was available to animals ad libitum throughout the study period. Water analyses are performed twice per year and include analyses of heavy metals and dissolved minerals. The CAs for water analysis were retained.

There are no known constituents in the feed or water interfered with the purpose or conduct of this study.

Cage and Animal Identification

An identification number corresponding to sequentially numbered ear tags was assigned to each animal. Prior to the allocation of animals to treatment groups, cages were identified with a label with the following information; study number, species/strain, gender, cage number and ear tag number. After allocation to the treatment groups, the cage identification did not change.

Treatment of Groups

The 15 recipients were randomly divided into three groups (see Table 1). One group (n=5) received a fluocinolone-eluting 100 DL 5E pellet (FLU) in the same subcutaneous pocket in which the NP was placed (FLU-0 cm) although an additional incision and tunnel, placed 1.5 cm lateral, was created to match the other groups' condition. The 100 DL 5E pellets were 1 mm long×0.7 mm diameter cylinders that were designed to be stable in vivo for >60 days. A second group (n=5) received FLU in a separate subcutaneous pocket, 1.5 cm lateral (toward animal's left) to the pocket in which the NP was placed (FLU-1 cm). A final group received a control pellet in a subcutaneous pocket 1.5 cm lateral (left) to the pocket in which the NP was placed (Control). The control 100 DL 5E pellet did not elute fluocinolone or any active pharmaceutical.

TABLE 1

Treatment Groups

| Groups | Implant | Location of Implant | n |
| --- | --- | --- | --- |
| 1 | Fluocinolone-eluting 100 DL 5E + 10% PEG 1500 pellet | Same pocket as NP (FLU-0 cm) + empty sham pocket 1.5 cm away | 5 + 5* |
| 2 | Fluocinolone-eluting 100 DL 5E 10% PEG 1500 pellet | Separate pocket from NP, 1.5 cm away (FLU-1.5 cm) | 5 + 5* |
| 3 | Control pellet | Separate pocket from NP, 1.5 cm away (No FLU) | 5 + 5* |

*Second group are donor animals that were used for NP collection

Body Weight and Clinical Observations

Body weights were taken prior to surgery. In addition, animals were observed regularly for signs of ill health.

NP Donor Rat Surgery

Donor rats for the NP collection were humanely sacrificed with $CO_2$ overdose. The tail from the donor rat was removed and the NP was extracted from each disk. The NP was removed from a total of eight disks from a single donor rat, pooled for a single implantation, and weighed. The pooled NP was kept in a moist environment (saline-soaked gauze) to prevent desiccation.

NP Recipient Rat Surgery

Once the NP was collected from the donor rat, the recipient rat was placed under isoflurance anesthesia. A small incision, approximately 2 cm long, was made in the abdominal skin of the recipient rat, close to the axial midline and about 1.5 cm to the left of the sagittal midline, and a subcutaneous tunnel was created with a hemostat. The NP was placed in the SC pocket. The incision site was closed with vicryl 4-O sutures in a continuous running stitch. In all groups, a similar second incision was made on the rat's right side, contralateral to the first pocket. A fluocinolone pellet (Group 2), or control pellet (Group 3), or nothing (Group 1) was placed in this pocket. Each implant site was marked with a skin tattoo. The tunnels to the pockets were parallel tracks with the edge of the pockets about 1.5 cm from each other.

Terminal Blood Collection

Blood samples (at least 1.5 mL) were obtained from all animals via cardiac puncture. The animals were anesthetized with isoflurane prior to collection. Blood samples were collected in K2EDTA tubes and immediately placed on wet ice. The blood samples were centrifuged within 1 hour of collection, the plasma was extracted (at least 500 μL) and was stored in a −20° C. freezer until it was shipped on dry ice to the lab listed below for analysis. Sample shipment of 13 samples occurred within 7 business days of collection (2 had clotted and were excluded).

Euthanasia

Three days after NP implantation, the animals were humanely euthanized by $CO_2$ asphyxiation.

NP Retrieval

NP was collected and weighed from 4 animals per group (n=12). Briefly, the tattoo marking the surgical site of NP placement was identified. The overlying skin was opened to expose any residual NP. The NP was removed and directly placed in a weigh boat. When there was a pellet contained in the same pocket with the NP, it was removed before weighing.

Tissue Collection for Histology

The tissues surrounding the implants and NP were collected from one randomly selected animal per treatment group (n=3) for histologic evaluation. An area of tissue (body wall, subcutis and skin) encompassing both implant sites and approximately 1 cm of tissue surrounding the implant sites were collected as a single sample. The sample was placed on a flat surface and then placed in 10% neutral buffered formalin within 15 minutes of euthanasia and allowed to fix.

Histology

Once fixed, tissue samples were trimmed in such a manner as to obtain a single cross section through the adjacent implant or mock implant site and three sections (a cross section (4-5 mm) and two lateral sections) through the NP or NP plus implant site, depending on treatment group. Tissues were processed, paraffin embedded, sectioned and stained with H&E. Slides were read by a veterinary pathologist and assessed for inflammatory responses and extent of residual NP.

Results

Figure 3:
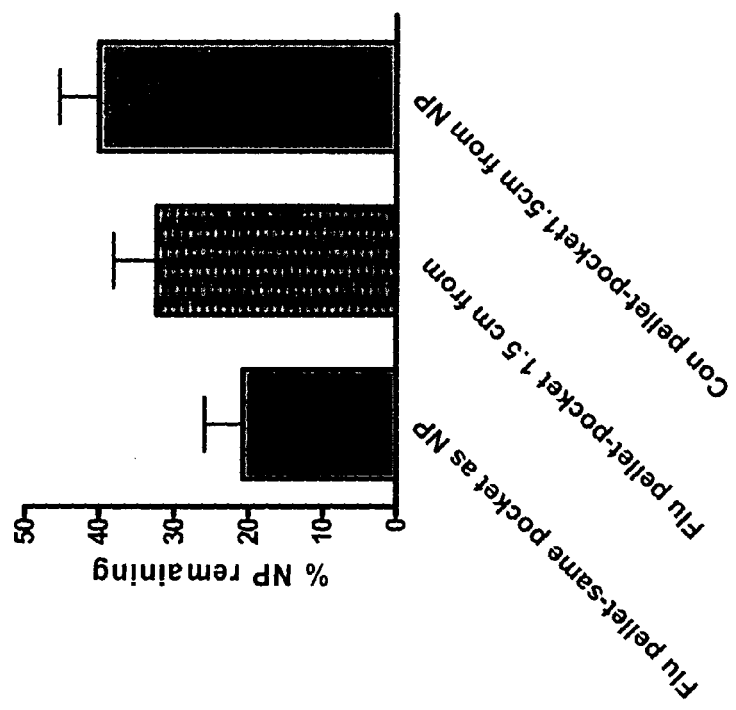
FIG. 3 is a bar graph illustration of the weight % of nucleus pulposus implanted and removed from rats that were divided into three treatment groups (one group with the drug depot containing fluocinolone in a poly(lactide-co-glycolide) (PLGA) placed 1.5 cm from the nucleus pulposus, one group with the drug depot containing fluocinolone in PLGA placed 0 cm from the nucleus pulposus and the third group with a control pellet). The fluocinolone enhanced nucleus pulposus resorption especially when placed next to the nucleus pulposus.

The weights of the NP implanted and removed from the pockets are presented in Table 2. The percent NP remaining was calculated for each animal and averaged for each treatment group. These data are graphed in FIG. 3 and the statistical analysis (1-way ANOVA) calculated. There appeared to be a trend indicating that fluocinolone may cause a reduction in the amount of NP remaining in the pocket after 3 days. A correlational analysis evaluating the relationship between the amount of NP implanted and the percentage of NP retrieved appeared to indicate that there was a trend for an inverse relationship (Pearson r=0.48). Notes from the surgeon indicated that for almost every animal, the consistency of the NP was thicker upon removal than at the time of implantation.

Discussion

The results from this study indicated that there was a trend toward increased resorption at 3-days post-implantation when the fluocinolone pellet was together with NP in the same pocket. By comparison, there was reduced resorption when a control pellet was present in a different pocket placed 1.5 cm from the NP pocket. The group of animals with the fluocinolone pellet in a distant pocket showed intermediate results for the % of NP remaining after 3 days. The histological findings seemed to correlate with these results, with the least amount of inflammatory infiltrate surrounding the NP when the fluocinolone was together in the same pocket and the greatest amount of inflammatory response in the animal implanted with the control pellet (which did not contain fluocinolone) on NP resorption.

Necropsy Information is indicated in Table 2 from the NP of different treatment groups (TG) is indicated below.

TABLE 2

| | | | | Necropsy Information | | | |
|---|---|---|---|---|---|---|---|
| TG | Donor ID | Recipient ID | Body Weight (g) | Wt of NP (mg) at Sx | Wt of NP (mg) at Nx | % of original NP WT | Necropsy Comments |
| 1 | 277 | 262 | 206.0 | 103.9 | 6.4 | 6.2 | NP appears thicker and less volume than when implanted FLU pellet was removed when weighing NP |
|  | 282 | 267 | 202.6 | 72.8 | ND |  |  |
|  | 283 | 268 | 201.9 | 75.9 | 16.6 | 21.9 | NP appears thicker and less volume than when implanted FLU pellet was removed when weighing NP |
|  | 288 | 273 | 194.6 | 68.7 | 16.4 | 23.0 | NP appears thicker than when implanted FLU pellet was removed when weighing NP |

TABLE 2-continued

Necropsy Information

| TG | Donor ID | Recipient ID | Body Weight (g) | Wt of NP (mg) at Sx | Wt of NP (mg) at Nx | % of original NP WT | Necropsy Comments |
|---|---|---|---|---|---|---|---|
|   | 289 | 274 | 202.9 | 68.1 | 21.2 | 31.1 | NP appears thicker than when implanted |
| 2 | 278 | 263 | 200.0 | 87.9 | 13.6 | 15.5 | NP appears thicker than when implanted |
|   | 281 | 266 | 203.3 | 86.5 | ND |  | NP appears slightly thicker than when implanted |
|   | 284 | 269 | 198.9 | 85.8 | 30.3 | 35.3 | NP appears thicker than when implanted |
|   | 287 | 272 | 206.8 | 51.9 | 20.3 | 39.1 | NP appears thicker than when implanted |
|   | 290 | 275 | 195.3 | 64.4 | 25.5 | 39.6 | NP appears thicker than when implanted |
| 3 | 279 | 264 | 196.9 | 69.7 | 18.7 | 26.8 | NP appears thicker and less volume than when implanted Control Pellet was removed when weighing NP |
|   | 280 | 265 | 212.8 | 59.6 | ND |  |  |
|   | 285 | 270 | 202.89 | 85.4 | 38.0 | 44.5 | NP appears thicker than when implanted |
|   | 286 | 271 | 196.98 | 78.1 | 40.4 | 51.7 | NP appears thicker than when implanted |
|   | 291 | 276 | 204.32 | 58.9 | 21.8 | 37.0 | NP appears slightly thicker than when implanted |

Example 2

Fluocinolone Formulations and Release Profiles

Fluocinolone is a potent steroid with glucocorticoid activity. To get consistent release the fluocinolone drug depots were made as described below. The drug depot contained 0.88 wt % fluocinolone, 10 wt % PEG 1500, and 88.22 wt % of 100 DL 5E that has ester end groups. The abbreviation "DL" refers to poly(DL-lactide). The drug depot had an average pellet diameter of 0.5 mm and the average pellet length was 2.02 mm.

It will be understood by those of ordinary skill in the art that other polymers may be used in the present application. For example, with drug loads of 1% fluocinolone, 85/15 PLGA or DL-PLA or DL-PLA and 50/50 PLGA mixtures can be added in an amount of from about 10% to 99%. Although in this study the average pellet diameter was 0.5 mm and the average pellet length was 2.02 mm, other depot can be extruded and made into other different sizes (e.g., 0.75 (length)×0.75 mm (diameter), 0.8×0.8 mm, 1×1 mm pellet sizes, etc.).

As to the polymers used in the depot, often times when the polymer is a heteropolymer or copolymer, there is a mixture of monomer species in the polymer. The mole ratio may be indicated and varied from 0:100 to 100:0 and ranges in between these mole ratios. For example, 85:15 DLG, the 85 refers to the monomer mole % 85 of DL (poly DL-lactide) in the polymer, while the 15 refers to the mole percent of the G (polyglycolide) in the polymer.

In the present application, the drug depot contained the polymer 100 DL. By way of example, 100 DL5E is a polymer that has an inherent viscosity of 0.45-0.55 dL/g. It contains 100% poly(DL-lactide) that has ester end groups. It is available from Lakeshore Biomaterials, Birmingham, Ala.

The fluocinolone pellets used in the study had the following weight and total dose listed in Table 3.

TABLE 3

Batch ID 00178-54

| Pellet Weight in Milligrams | Fluocinolone Dose in Micrograms |
|---|---|
| 0.69 | 6.07 |
| 0.67 | 5.90 |
| 0.65 | 5.72 |
| 0.67 | 5.90 |
| 0.62 | 5.46 |
| 0.57 | 5.02 |
| 0.55 | 4.84 |
| 0.58 | 5.10 |
| 0.60 | 5.28 |
| 0.59 | 5.19 |
| 0.68 | 5.98 |
| 0.65 | 5.72 |
| 0.66 | 5.81 |
| 0.62 | 5.46 |
| 0.57 | 5.02 |
| 0.59 | 5.19 |

Average Pellet Diameter: 0.54 +/− 0.03 mm
Average pellet length 2.02 +/− 0.05 mm These drug depots were tested for their in vitro release profile. FIG. 4 is a graphic representation of in vitro % cumulative release profile of a drug depot containing 0.88 wt % (~1%) fluocinolone, 10 wt % PEG 1500, and 88.22 wt % of 100 DL that has ester end groups 1 wt % fluocinolone, 10 wt % PEG 1500, and 89 wt % of 100% DL. The drug depot elutes 0.0025 to about 0.0125 mcg/day for over 60 days and releases at least 40% of fluocinolone loaded in the drug depot over 60 days. This is one example of an ideal release profile that may be used to treat intervertebral disc herniation.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of treating intervertebral disc herniation in a patient in need of such treatment, the method comprising administering one or more biodegradable drug depots comprising a therapeutically effective amount of a glucocorticoid through a tear in an annulus fibrosis and into a nucleus pulposus of the intervertebral disc herniation, wherein a portion of the nucleus pulposus is leaving the tear, and the one or more biodegradable drug depots does not contain fibrin and is capable of releasing an effective amount of the glucocorticoid over a period of at least 3 days to 6 months, the one or more drug depots comprising a polymer having an inherent viscosity of 0.45 dL/g to 0.55 dL/g, the polymer comprising poly(DL-lactide) having ester end groups and the glucocorticoid is fluocinolone in an amount of about 0.5% to 20% by weight based on the total weight of the drug depot, and the fluocinolone has a particle size from about 10 μm to 100 μm, and the one or more biodegradable drug depots comprises mPEG.

2. A method according to claim 1, wherein the one or more drug depots reduces size of the herniation by at least 20% by enhancing resorption of the nucleus pulposus.

3. A method according to claim 1, wherein the one or more drug depots reduces size of the herniation by at least 50% by enhancing resorption of the nucleus pulposus.

4. A method according to claim 1, wherein the one or more drug depots releases an effective amount of the fluocinolone over a period of at least 3 days to 6 weeks.

5. A method according to claim 4, wherein the one or more drug depots releases 0.002 mcg to 0.02 mcg of fluocinolone every 24 hours for a period of at least 1 week to 6 weeks.

6. A method according to claim 1, wherein the one or more drug depots releases 5%, 10%, 15%, 20%, 25%, 30%, 40%, 50%, 60%, 70%, 80%, 90%, 95%, or 99% of the glucocorticoid relative to a total amount of glucocorticoid loaded in the drug depot over a period of at least 1 week to 6 weeks after the drug depot is administered.

7. A method according to claim 1, wherein the glucocorticoid is encapsulated in a plurality of depots comprising microparticles, microspheres, microcapsules, and/or microfibers suspended in a gel.

8. A method according to claim 1, wherein the one or more drug depots is administered before, during or after surgery.

9. A method according to claim 1, wherein a barrier is administered before, after or with the one or more drug depots at or near the intervertebral disc herniation.

10. An implantable drug depot useful for treating intervertebral disc herniation in a patient in need of such treatment, the implantable drug depot comprising fluocinolone in an amount of about 0.5% to 20% by weight based on the total weight of the drug depot, the depot implanted to be through a tear in an annulus fibrosis and into a nucleus pulposus of the intervertebral disc herniation, the drug depot comprising a polymer having an inherent viscosity of 0.45 dL/g to 0.55 dL/g, the polymer comprising poly(DL-lactide) having ester end groups, and wherein the depot has a modulus of elasticity in the range of about $1\times10^4$ to about $6\times10^5$ dynes/cm$^2$ after the depot is implanted into the nucleus pulposus of the intervertebral disc herniation, and the fluocinolone has a particle size from about 10 μm to 100 μm, and the implantable drug depot comprises mPEG.

11. An implantable drug depot according to claim 10, wherein the drug depot comprises the polymer in an amount of from about 10% to about 99% by weight based on the total weight of the drug depot.

12. A method of reducing the size of an intervertebral disc herniation in a patient, the method comprising administering one or more biodegradable drug depots comprising 1 wt % to about 20 wt % of fluocinolone through a tear in an annulus fibrosis and into a nucleus pulposus of the intervertebral disc herniation, wherein a portion of the nucleus pulposus is leaving the tear, and the one or more biodegradable drug depots does not contain fibrin and is capable of releasing fluocinolone over a period of at least 3 days to two months to reduce the size of the intervertebral disc herniation by at least 50%, wherein the drug depot comprises a polymer having an inherent viscosity of 0.45 dL/g to 0.55 dL/g, the polymer comprising poly(DL-lactide) having ester end groups, and wherein the one or more biodegradable drug depots have a modulus of elasticity in the range of about $1\times10^4$ to about $6\times10^5$ dynes/cm$^2$ after the one or more biodegradable drug depots are administered into the nucleus pulposus of the intervertebral disc herniation, and the fluocinolone has a particle size from about 10 μm to 100 μm, and the one or more biodegradable drug depots comprises mPEG.

13. A method according to claim 1, wherein the one or more drug depots have a modulus of elasticity in the range of about $2\times10^4$ to about $5\times10^5$ dynes/cm$^2$ after the one or more drug depots are administered into the nucleus pulposus of the intervertebral disc herniation.

14. A method according to claim 1, wherein the one or more drug depots have a modulus of elasticity in the range of about $5\times10^4$ to about $5\times10^5$ dynes/cm$^2$ after the one or more drug depots are administered into the nucleus pulposus of the intervertebral disc herniation.

15. An implantable drug depot according to claim 10, wherein the depot has a modulus of elasticity in the range of about $2\times10^4$ to about $5\times10^5$ dynes/cm$^2$ after the depot is implanted into the nucleus pulposus of the intervertebral disc herniation.

16. An implantable drug depot according to claim 10, wherein the depot has a modulus of elasticity in the range of about $5\times10^4$ to about $5\times10^5$ dynes/cm$^2$ after the depot is implanted into the nucleus pulposus of the intervertebral disc herniation.

17. An implantable drug depot according to claim 10, wherein the implantable drug depot has a modulus of elasticity of about $5\times10^4$ dynes/cm$^2$ after the depot is implanted into the nucleus pulposus of the intervertebral disc herniation.

18. An implantable drug depot according to claim 10, wherein the implantable drug depot comprises fluocinolone acetonide in an amount of about 0.5% to 3.0% by weight.

19. A method according to claim 1, wherein the one or more biodegradable drug depots comprises an immediate release layer and a sustained release layer, and a viscosity enhancing agent.

* * * * *

UNITED STATES PATENT AND TRADEMARK OFFICE
CERTIFICATE OF CORRECTION

PATENT NO. : 9,492,461 B2
APPLICATION NO. : 12/396122
DATED : November 15, 2016
INVENTOR(S) : King et al.

Page 1 of 2

It is certified that error appears in the above-identified patent and that said Letters Patent is hereby corrected as shown below:

In the Specification

In Column 1, Line 9, delete "2008," and insert -- 2008, now Pat. No. 8,524,267, --, therefor.

In Column 9, Line 1, delete "semipimod" and insert -- semapimod --, therefor.

In Column 9, Line 29, delete "IL-II" and insert -- IL- 11 --, therefor.

In Column 9, Lines 49-50, delete "[2-hydroxy-5-[-4-[C2-pyridinylamino)sulfonyl]azo]benzoic acid]" and insert -- "[2-hydroxy-5-[[-4-[(2-pyridinylamino)sulfonyl]phenyl]azo]benzoic acid] --, therefor.

In Column 9, Line 58, delete "bupivicaine," and insert -- bupivacaine, --, therefor.

In Column 10, Line 39, delete "lower then" and insert -- lower than --, therefor.

In Column 10, Line 66, delete "15, %," and insert -- 15%, --, therefor.

In Column 12, Line 54, delete "polyphosphagenes," and insert -- polyphosphazenes, --, therefor.

In Column 12, Lines 57-58, delete "L-lactide, ,-caprolactone," and insert -- L-lactide-caprolactone, --, therefor.

In Column 12, Line 63, delete "PEG-PLG," and insert -- PEG-PLGA, --, therefor.

In Column 13, Line 64, delete "fourth," and insert -- forth --, therefor.

In Column 15, Line 37, delete "polyphosphagenes," and insert -- polyphosphazenes, --, therefor.

Signed and Sealed this
Twenty-first Day of February, 2017

Michelle K. Lee
*Director of the United States Patent and Trademark Office*

CERTIFICATE OF CORRECTION (continued)
U.S. Pat. No. 9,492,461 B2

In Column 15, Line 41, delete "L-lactide, ,-caprolactone," and insert -- L-lactide-caprolactone, --, therefor.

In Column 15, Line 45, delete "PEG-PLG" and insert -- PEG-PLGA --, therefor.

In Column 16, Line 21, delete "faster and than" and insert -- faster than --, therefor.

In Column 23, Line 62, delete "annular tears, 22a" and insert -- annular tears 25a --, therefor.

In Column 24, Lines 6-7, delete "annular tears 28," and insert -- annular tears 25b, --, therefor.

In Column 28, Line 34, delete "PGLA" and insert -- PLGA --, therefor.

In Column 28, Line 40, delete "PGLA" and insert -- PLGA --, therefor.